United States Patent
Sawai et al.

(10) Patent No.: US 8,859,260 B2
(45) Date of Patent: Oct. 14, 2014

(54) EXPRESSION CASSETTE FOR LACTASE DEHYDROGENASE, TRANSFORMED YEAST AND METHOD OF PRODUCING LACTIC ACID

(75) Inventors: Kenji Sawai, Kanagawa (JP); Hideki Sawai, Kanagawa (JP)

(73) Assignee: Toray Industries, Inc. (JP)

( * ) Notice: Subject to any disclaimer, the term of this patent is extended or adjusted under 35 U.S.C. 154(b) by 546 days.

(21) Appl. No.: 12/746,642

(22) PCT Filed: Dec. 5, 2008

(86) PCT No.: PCT/JP2008/072129
§ 371 (c)(1),
(2), (4) Date: Jun. 7, 2010

(87) PCT Pub. No.: WO2009/072593
PCT Pub. Date: Jun. 11, 2009

(65) Prior Publication Data
US 2010/0273225 A1 Oct. 28, 2010

(30) Foreign Application Priority Data

Dec. 7, 2007 (JP) ................................. 2007-317566

(51) Int. Cl.
*C12N 1/19* (2006.01)
*C12N 9/04* (2006.01)
*C12P 7/56* (2006.01)
*C12N 15/81* (2006.01)

(52) U.S. Cl.
CPC .................. *C12P 7/56* (2013.01); *C12N 9/0006* (2013.01); *C12N 15/81* (2013.01)
USPC ..................................................... 435/254.2

(58) Field of Classification Search
None
See application file for complete search history.

(56) References Cited

U.S. PATENT DOCUMENTS

| 6,429,006 | B1 | 8/2002 | Porro et al. |
| 7,696,333 | B1 | 4/2010 | Ishida et al. |
| 2003/0166179 | A1 | 9/2003 | Rajgarhia et al. |
| 2009/0239274 | A1* | 9/2009 | Sawai et al. ................ 435/139 |
| 2009/0269812 | A1 | 10/2009 | Sawai et al. |

FOREIGN PATENT DOCUMENTS

| JP | 2001-516584 T | 10/2001 | |
| JP | 2003-093060 A1 | 4/2003 | |
| JP | 2003-265177 A | 9/2003 | |
| JP | 02003265177 | * 9/2003 | ............ C12N 15/09 |
| JP | 02003265177-MT | * 9/2003 | ............ C12N 15/09 |
| JP | 2005-137306 A | 6/2005 | |
| JP | 2005-245335 A | 9/2005 | |
| JP | 2005-528106 A | 9/2005 | |
| JP | 2006-288318 A | 10/2006 | |
| JP | 2006-296377 A | 11/2006 | |
| JP | 2007-020538 A | 2/2007 | |
| JP | 2007-082490 A | 4/2007 | |
| WO | 99/14335 A1 | 3/1999 | |
| WO | 02/064240 A1 | 8/2002 | |
| WO | 03/102152 A2 | 12/2003 | |
| WO | 2007/043253 A1 | 4/2007 | |
| WO | WO2007043253 | * 4/2007 | ............ C12N 15/09 |
| WO | 2007/097260 A1 | 8/2007 | |
| WO | WO2010140602 | * 12/2010 | ............ C12N 15/09 |

OTHER PUBLICATIONS

Ishida et al, D-lactic acid production by metabolically engineered *Saccharomyces cerevisiae*. J Biosci Bioeng. Feb. 2006;101(2):172-7.*
N_Geneseq_201215 database Acc# AFU72952 from Sawai et al, WO2007043253 Apr. 19, 2007. Alignment with SEQ ID No. 4.*
N_Geneseq_201215 database Acc#BD359264 from Sahara et al, JP02003265177 Sep. 24, 2003. Alignment with SEQ ID No. 1.*
McConaughy et al, Nucleic acid reassociation in formamide. Biochemistry Aug. 1969;8(8):3289-95.*
N_Geneseq_201215 database Acc#AYM54212 from Sawai et al, WO2010140602 Dec. 9, 2010. Alignment with SEQ ID No. 1.*
Nobuhiro Ishida et al., "D-Lactic Acid Production by Metabolically Engineered *Saccharomyces cerevisiae*," Journal of Bioscience and Bioengineering, vol. 101, No. 2, 2006, pp. 172-177.
Miho Kawahata et al., "Yeast genes involved in response to lactic acid and acetic acid: acidic conditions caused by the organic acids in *Saccharomyces cerevisiae* cultures induce expression of intracellular metal metabolism genes regulated by Aft 1p," FEMS Yeast Res, vol. 6, No. 6, 2006, pp. 924-936.

* cited by examiner

*Primary Examiner* — Sheridan Swope
(74) *Attorney, Agent, or Firm* — DLA Piper LLP (US)

(57) ABSTRACT

A gene expressing cassette codes lactate dehydrogenase that is needed for prevention of deterioration in lactic acid yield and lactic acid production rate in continuous culture with simultaneous filtration of a yeast strain having a lactic acid-producing ability, which achieves high optical purity, high lactic acid yield and high lactic acid production rate simultaneously, a yeast strain having the cassette and a method of producing lactic acid by culturing the yeast strain. The lactate dehydrogenase-expressing cassette is a lactate dehydrogenase-expressing cassette, comprising a gene coding lactate dehydrogenase connected to a site downstream of a promoter, the promoter being a promoter of a gene showing a gene expression amount larger by 5 times or more than the average relative expression amount of all genes after 50 hours from start of culture in continuous culture with simultaneous filtration of a yeast strain having a lactic acid-producing ability.

7 Claims, 5 Drawing Sheets

1 fermentation reaction tank
2 separation membrane element
3 head-difference control unit
4 gas-supplying apparatus
5 stirrer
6 level sensor
7 medium-supplying pump
8 pH-adjusted solution supply pump
9 pH sensor-control unit
10 temperature controller 1 fermentation reaction tank
2 separation membrane element
3 head-difference control unit
4 gas-supplying apparatus
5 stirrer
6 level sensor
7 medium-supplying pump
8 pH-adjusted solution supply pump
9 pH sensor-control unit
10 temperature controller
11 fermentation culture solution-circulating pump
12 membrane separation tank 13 rigid supporting plate
14 channel material
15 separation membrane
16 dent
17 water-collecting pipe 18 bundle of hollow-fiber separation membranes
19 top resin-sealing layer
20 bottom resin-sealing layer
21 supporting frame
22 water-collecting pipe

US 8,859,260 B2

EXPRESSION CASSETTE FOR LACTASE DEHYDROGENASE, TRANSFORMED YEAST AND METHOD OF PRODUCING LACTIC ACID

RELATED APPLICATIONS

This is a §371 of International Application No. PCT/JP2008/072129, with an international filing date of Dec. 5, 2008 (WO 2009/072593 A1, published Jun. 11, 2009), which is based on Japanese Patent Application No. 2007-317566, filed Dec. 7, 2007, the subject matter of which is incorporated by reference.

TECHNICAL FIELD

This disclosure relates to a lactate dehydrogenase-expressing cassette, a transformant yeast strain containing the cassette and a method of producing lactic acid comprising culturing the yeast strain, more specifically, a lactate dehydrogenase-expressing cassette higher in lactic acid production efficiency, a transformant yeast strain containing the cassette and a method of producing lactic acid comprising culturing the yeast strain.

BACKGROUND

Recently, polymers that are prepared by using biomasses such as plants as raw material are attracting attention in a trend toward establishment of a resource-circulating society. In particular, polylactic acid (hereinafter, referred to as "PLA") was shown to have favorable properties as a polymer from biomass raw material.

Lactic acid, the raw material for PLA, is produced by fermentation of microbes, generally called lactic bacteria, represented by those of *Lactobacillus species* and *Lactococcus species*. Production of lactic acid by using lactic bacteria is superior in lactic acid yield from sugar and lactic acid production rate. However, the lactic acid obtained is a mixture of L- and D-lactic acids. Thus, there is a problem in optical purity. High optical purity is demanded for the lactic acid for use in production of PLA.

There were several attempts to produce high-optical purity lactic acid. For example, production of L- and D-lactic acids by using a transformant yeast strain was studied (for example, JP 2001-516584 A, JP 2003-093060 A, JP 2005-137306 A and N. Ishida et al., J. Biosci. Bioeng., 101(2), pp. 172-177, 2006). Yeasts do not have ability to produce lactic acid inherently. It was reported in these literatures that high-optical purity lactic acid could be obtained by introducing a gene coding lactate dehydrogenase, which converts pyruvic acid into lactic acid, into yeast by genetic recombination technology. On the other hand, the lactic acid yield and the lactic acid production rate during lactic acid production by yeast are lower, compared to those by lactic bacteria. It is thus needed to improve both lactic acid yield and lactic acid production rate for production of lactic acid by using a yeast at low cost.

For improvement of the lactic acid yield and the lactic acid production rate at the same time, a method of culturing a yeast strain having a lactic acid-producing ability while the fermentation solution is filtered through a separation membrane was developed (see, for example, WO 2007/97260). However, even if the method was used, it caused a problem that both the lactic acid yield and the lactic acid production rate declined during fermentation.

It could therefore be helpful to provide a gene expressing cassette coding lactate dehydrogenase that is needed for prevention of deterioration in lactic acid yield and lactic acid production rate in continuous culture with simultaneous filtration of a yeast strain having a lactic acid-producing ability, which achieves high optical purity, high lactic acid yield and high lactic acid production rate simultaneously, a yeast strain having the cassette and a method of producing lactic acid by culturing the yeast strain.

SUMMARY

We found that it was possible to carry out continuous culture consistently for an extended period of time without deterioration in lactic acid yield and lactic acid production rate, by culturing a yeast strain having a lactate dehydrogenase-expressing cassette containing a promoter of a gene showing a gene expression amount larger by 5 times or more than the average relative expression amount of all genes after 50 hours from start of culture while filtering the yeast through a separation membrane, in continuous culture with simultaneous filtration by separation membrane of a yeast strain having a lactic acid-producing ability.

We thus provide a lactate dehydrogenase-expressing cassette, comprising a gene coding lactate dehydrogenase connected to a site downstream of a promoter, the promoter being a promoter of a gene showing a gene expression amount larger by 5 times or more than the average relative expression amount of all genes after 50 hours from start of culture in continuous culture with simultaneous filtration of a yeast strain having a lactic acid-producing ability. Preferably, the promoter is the promoter of suppression-of-exponential-defect 1 gene (SED1 gene), cell-wall-associated protein 2 gene (CWP2 gene) or enolase 1 gene (ENO1 gene), more preferably, a promoter having a nucleotide sequence selected from the following sequences (a) to (c):

(a) a promoter having the nucleotide sequence shown by any one of SEQ ID Nos. 1 to 3;
(b) a promoter having a nucleotide sequence that hybridizes with the nucleotide sequence shown by any one of SEQ ID Nos. 1 to 3 or a nucleotide sequence having part of it under stringent condition; and
(c) a promoter having a nucleotide sequence obtained by deletion, substitution and/or insertion of one or more bases from the nucleotide sequence shown by any one of SEQ ID Nos. 1 to 3.

We also provide a lactate dehydrogenase-expressing cassette containing a promoter selected from the following group (a) and a gene coding lactate dehydrogenase selected from the following group (b):

(a)
(1) a promoter having the nucleotide sequence shown by any one of SEQ ID Nos. 1 to 3;
(2) a promoter having a nucleotide sequence that hybridizes with the nucleotide sequence shown by any one of SEQ ID Nos. 1 to 3 or a nucleotide sequence containing part of it under stringent condition; and
(3) a promoter having a nucleotide sequence obtained by deletion, substitution and/or insertion of one or more bases from the nucleotide sequence shown by any one of SEQ ID Nos. 1 to 3, and (b)
(1) a gene coding lactate dehydrogenase having the nucleotide sequence shown by any one of SEQ ID Nos. 4 to 6;
(2) a gene coding lactate dehydrogenase having a nucleotide sequence that hybridize with the nucleotide sequence shown by any one of SEQ ID Nos. 4 to 6 or a nucleotide sequence containing part of it under stringent condition; and (3) a gene coding lactate dehydrogenase having a nucleotide sequence obtained by deletion, substitution and/or addition of one or more bases from the nucleotide sequence shown by any one of SEQ ID Nos. 4 to 6.

We further provide a transformant yeast strain, comprising at least one lactate dehydrogenase-expressing cassette described above on chromosome. Preferably, it is a yeast in which at least one gene selected from suppression-of-exponential-defect 1 gene (SED 1 gene), cell-wall-associated protein 2 gene (CWP2 gene) and enolase 1 gene (ENO1 gene) is substituted with the lactate dehydrogenase-expressing cassette.

The transformant yeast strain preferably belongs to Genus *Saccharomyces*. The transformant yeast strain is more preferably *Saccharomyces cerevisiae*.

We still further provide a method of producing lactic acid comprising a culture step of culturing the transformant yeast strain. Preferably, the culture step is continuous fermentation of filtering the culture solution through a separation membrane, recovering lactic acid from the filtrate, holding or feeding back the unfiltered solution to the culture solution, and adding the medium to the culture solution.

A yeast strain having a lactate dehydrogenase-expressing cassette containing the promoter of a gene showing a gene expression amount larger by 5 times or more than the average relative expression amount of all genes after 50 hours from start of culture is cultured, while the culture solution is filtered through a separation membrane, in continuous culture with simultaneous filtration of the yeast strain having a lactic acid-producing ability. It is possible as a result to produce high-optical purity lactic acid at high yield and high production rate consistently for an extended period of time.

EXPLANATION OF REFERENCES

Figure 1:
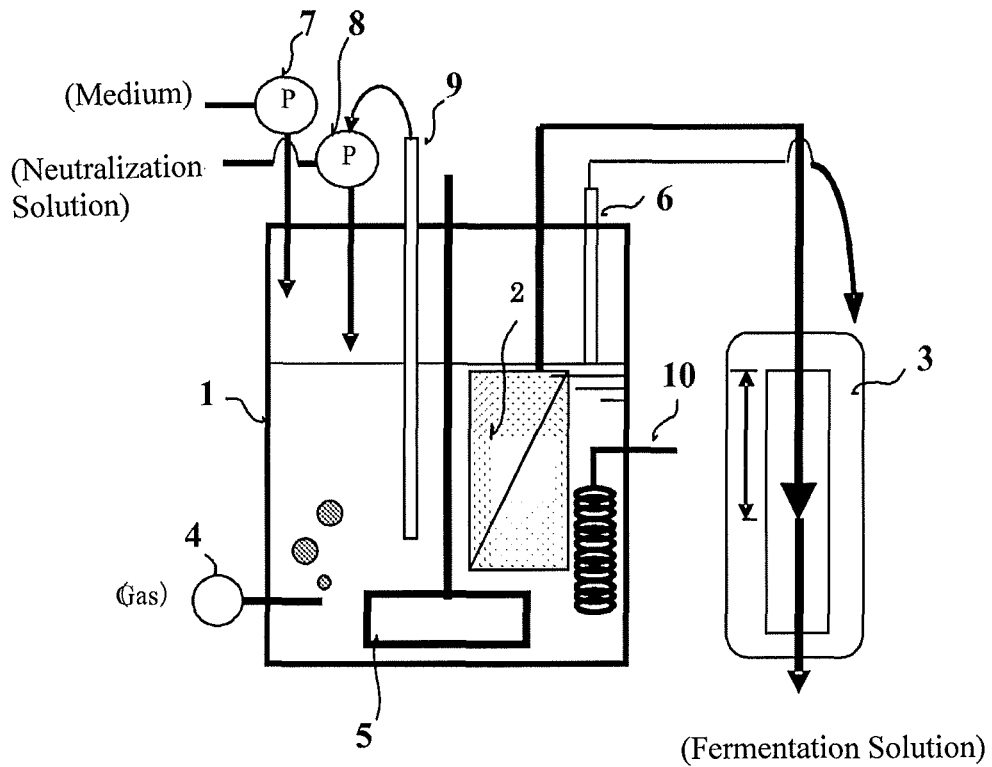
FIG. 1 is a schematic side view explaining a membrane-separation continuous fermentation apparatus.

1: Fermentation reaction tank
2: Separation membrane element 2
3: Head-difference control unit
4: Second tag sequence
5: Agitator
6: Level sensor
7: Medium-supplying pump
8: Ph-adjusted solution supply pump
9: Ph sensor-control unit
10: Temperature controller
11: Fermentation culture solution-circulating pump
12: Membrane separation tank
13: Supporting plate
14: channel material
15: Separation membrane
16: Dent
17: Water-collecting pipe
18: Separation membrane bundle
19: Top resin-sealing layer
20: Bottom resin-sealing layer
21: Supporting frame
22: Water-collecting pipe
P: Pump

DETAILED DESCRIPTION

Lactate Dehydrogenase-Expressing Cassette

The lactate dehydrogenase-expressing cassette is a lactate dehydrogenase (herein-after, referred to as "LDH")-expressing cassette, in which a gene coding lactate dehydrogenase (ldh gene) is connected to a site downstream of the promoter thereof, wherein, the promoter is a gene promoter having a gene expression amount larger by 5 times or more than the average relative expression amount of all genes after 50 hours from start of culture, in continuous culture with simultaneous filtration by separation membrane of a yeast strain having a lactic acid-producing ability.

The "ldh gene" is a gene coding LDH having an activity to convert reduced nicotinamide adenine dinucleotide (NADH) and pyruvic acid to oxidized nicotinamide adenine dinucleotide (NAD+) and L-lactic acid or NAD+ and D-lactic acid.

The ldh gene is not particularly limited, if it is a gene coding LDH having the activity described above, but it is preferably a ldh gene derived from a microbe such as lactic bacterium or *Bacillus subtilis* or a ldh gene derived from an eukaryotic organism such as human, bovine, frog or malaria. Particularly favorable are genes derived from microbes such as *Lactobacillus casei, Lactobacillus plantarum, Lactobacillus bulgaricus, Lactobacillus sasei, Lactobacillus delbrueckii, Lactobacillus johnsonii, Lactobacillus helveticus, Lactobacillus curvatus, Lactobacillus bacillus acidophilus, Leuconostoc mesenteroides, Leuconostoc lactis, Lactococcus lactis, Pediococcus pentosaceus, Pediococcus acidilactici, Bacillus subtilis* and *Bacillus stearothermophilus*. Examples of the ldh genes derived from eukaryotic organisms favorably used include those derived from *Rhizopus oryzae, Homo sapiens, Bos taurus, Xenopus laevis, Canis familiaris, Alligator mississippiensis, Monodelphis domestica, Pelodiscus sinensis, Squalus acanthias, Plamodium falciparum, Plamodium vivax, Plamodium marariae* and *Plamodium ovale*.

The ldh genes include mutant genes for example caused by genetic polymorphism and mutagenesis. The genetic polymorphism, as used herein, is partial change of the nucleotide sequence of a gene caused by natural mutation of the gene. Alternatively, the mutagenesis is artificial mutation of a gene, and performed, for example, by a method of using a site-specific mutation kit (Mutan-K (manufactured by Takara Bio Inc.)) or a method of using a random mutation kit (BD Diversify PCR Random Mutagenesis (manufactured by CLON-TECH)).

The method of cloning the ldh gene is not particularly limited, and any known method may be used. Examples thereof include a method of amplifying and obtaining a desired gene region by PCR (Polymerase Chain Reaction), based on known gene information, a method of cloning it by using homology and enzyme activity in genome libraries and cDNA libraries as indicators, and the like. Alternatively, it may be prepared by chemical synthesis or genetic engineering, based on known protein information.

The lactate dehydrogenase (LDH) expression cassette is not particularly limited, if it is a nucleotide sequence that can express LDH from the ldh gene, via mRNA, in the cells containing the LDH-expressing cassette. Preferably, it is a nucleotide sequence having a promoter, a ldh gene and a terminator as they are aligned continuously. The terminator, as used herein, means a sequence that terminates mRNA transcription of the gene and is normally a 3 terminal-sided downstream sequence of the gene present on chromosome.

The "yeast strain having a lactic acid-producing ability" is a yeast that can produce lactic acid by consumption of sugars such as glucose, sucrose, fructose and so on, preferably, a yeast containing an ldh gene introduced by genetic recombination.

Hereinafter, the method of introducing a ldh gene into yeast will be described. The ldh gene is introduced into yeast, for example, by a method of transforming a yeast with a ldh gene expression vector containing a ldh gene recombined into the expression vector, a method of inserting a ldh gene at a desired position of chromosome by homologous recombination, or a method of inserting a ldh gene into chromosome at random by heterologous recombination.

Expression vectors commonly used in yeast can be used as the expression vectors for recombination of the ldh gene. The expression vector commonly used in yeast has a sequence needed for autonomous replication in yeast cells, a sequence needed for autonomous replication in *Escherichia coli* cells, a yeast selectable marker and an *Escherichia coli* selectable marker, and preferably has additionally so-called regulatory sequences regulating the expression of the recombinant ldh gene such as of operator, promoter, terminator and enhancer.

The sequence needed for autonomous replication in yeast cells is, for example, the sequence in combination of a yeast autonomous replicating sequence (ARS1) and a centromere sequence or the sequence of the replication origin of a yeast 2 μm plasmid. The sequence needed for autonomous replication in *Escherichia coli* is, for example, the sequence of the ColE1 replication origin of *Escherichia coli*. Alternatively, examples of the yeast selectable markers include auxotrophic complementary gene such as URA3 and TRP 1 and drug-resistance genes such as G418 resistance gene and neomycin resistance gene. Examples of the *Escherichia coli* selectable marker include antibiotic resistance genes such as ampicillin resistance gene and kanamycin resistance gene. The regulatory sequence is not particularly limited, if it is a sequence that can express the ldh gene, and examples thereof include promoter sequences such as of acid phosphatase gene (PHO5), glyceraldehyde-3-phosphate dehydrogenase genes (TDH1, 2 and 3), alcohol dehydrogenase genes (ADH1, 2, 3, 4, 5, 6 and 7), galactose metabolism-related genes (GAL1, 7 and 10), cytochrome c gene (CYC1), triosephosphate isomerase gene (TPI1), phosphoglycerate kinase gene (PGK1), phosphofructose kinase gene (PFK1), pyruvate decarboxylase genes (PDC1, 5 and 6) and terminator sequences such as of TDH3 gene. However, the expression vector is not limited thereto.

It is possible to obtain a vector capable of expressing a ldh gene by introducing the ldh gene at a site downstream of the promoter of the expression vector. It is possible to introduce the ldh gene into yeast by transforming the yeast with the ldh gene expression vector obtained by the method described below.

It is also possible to introduce a ldh gene into yeast by inserting the ldh gene into chromosome. The method of inserting the ldh gene into chromosome is not particularly limited, but the ldh gene can be inserted, for example, by a method of transforming yeast with a ldh gene-containing DNA by the method described below and inserting the ldh gene at a random position in chromosome by heterologous recombination or by a method of inserting a ldh gene-containing DNA at a desirable position by homologous recombination. It is preferably the method by homologous recombination.

The method of inserting a ldh gene-containing DNA at a desired position in chromosome by homologous recombination is, for example, a method of performing PCR by using a primer designed to add a homologous region at desired positions upstream and downstream of the ldh gene-containing DNA and transforming a yeast with the PCR fragments obtained by the method described below, but is not limited thereto. In addition, the PCR fragment preferably contains a yeast selectable marker for easy selection of the transformant.

The PCR fragment for use is prepared, for example, in the steps of 1 to 3, as shown below in (1) to (3). Here, a method of introducing a ldh gene at a position downstream of the promoter of pyruvate decarboxylase 1 gene (PDC1 gene) will be described as an example.

(1) Step 1: A fragment containing a ldh gene and a terminator is amplified by PCR, by using a template of a plasmid having a terminator connected downstream of a ldh gene as template and a set of primers 1 and 2. Here, the primer 1 is designed to add a homologous sequence of 40 bp or more at a position upstream of the PDC 1 gene, while the primer 2 is designed, based on the plasmid-derived sequence downstream of the terminator.

(2) Step 2: A fragment containing a yeast selectable marker is amplified by PCR, by using a yeast selectable marker-containing plasmid, such as pRS424 or pRS426, as template and a set of primers 3 and 4. Here, the primer 3 is designed to add a sequence of 30 bp or more that is homologous to the sequence downstream of the terminator in the PCR fragment of Step 1, while the primer 4 is designed to add a sequence of 40 bp or more that is homologous to the downstream side of the PDC1 gene.

(3) Step 3: A PCR fragment containing a ldh gene, a terminator and a yeast selectable marker, to which the sequences corresponding to the upstream and downstream sides of the PDC 1 gene are added at both terminals, is obtained by preforming PCR by using a mixture of the PCR fragments obtained in Steps 1 and 2 as template and a set of primers 1 and 4.

Preferably for introduction of the LDH-expressing cassette into chromosome, a plasmid carrying a any promoter, a ldh gene and a terminator is used as the PCR template plasmid used in the Step 1, and the primer 1 is designed to add a homologous sequence of 40 bp or more at a desired introduction position for amplification of the promoter, the ldh gene and the terminator.

A method, for example, of transformation, transduction, transfection, cotransfection or electroporation may be used for introduction of the ldh gene expression vector or the PCR fragment thus obtained into yeast. Typical examples thereof include a method of using lithium acetate, a protoplast method, and the like.

The transformant obtained may be cultured by any known method, for example, by the method described in "M. D. Rose et al., "Methods in Yeast Genetics", Cold Spring Harbor Laboratory Press (1990)." The yeast carrying the ldh gene expression vector or the PCR fragment introduced may be selected, based of the yeast selectable marker contained in the expression vector or the PCR fragment, when the yeast is cultured in a nutrient-free medium or a drug-added medium.

"Continuous culture with simultaneous filtration" means continuous culture in which the culture solution is filtered through a separation membrane, the product is recovered from the filtrate, the unfiltered solution is held in or sent back to the culture solution, and raw fermentation materials are added to the culture solution. The separation membrane for use is preferably a porous membrane that is resistant to clogging by the yeast used in culture and thus gives favorable filtration performance consistently for an extended period of time. The material for the separation membrane is a ceramic material or an organic polymer, preferably an organic polymer.

Hereinafter, the "gene expressed in a gene expression amount larger by 5 times or more than the average relative expression amount of all genes" will be described. The gene expression amount means the amount of the messenger RNA (mRNA) transcripted from a gene, and the average relative expression amount of all genes is the average expression amount of preferably all genes registered in *Saccharomyces* Genome Database, but one or more genes may be missing. Thus, the "gene expressed in a gene expression amount larger by 5 times or more than the average relative expression amount of all genes" means a gene that is transcripted to its mRNA in an amount larger by 5 times or more than the average amount of the mRNAs of all genes. Because this disclosure is characterized by use of a promoter of a gene having a larger gene expression amount, the gene is preferably a gene that is expressed in a gene expression amount larger by 7 times or more, more preferably 10 times or more, than the average relative expression amount of all genes.

Examples of the method of determining the average relative expression amount of all genes include Northern blotting method, qPCR (quantitative PCR) method, real-time PCR method, DNA microarray method and the like. Although the former three methods are methods normally for measuring the expression amounts of individual genes, the DNA microarray method is a method of measuring the expression amount of all genes present on an array by means of hybridization of a probe immobilized on the array with previously fluorescent-labeled mRNAs and measurement of the fluorescence intensity with a special scanner, and for that reason, use of the DNA microarray method is preferable. During measurement of the fluorescence intensity with a scanner, it is desirable to measure it at a laser intensity at which the number of the spots showing saturation of the fluorescence intensity can be reduced as much as possible and the entire fluorescence intensity can be raised. Such laser intensity, which varies according to the test sample, can be determined by simple examination.

The DNA microarray is not particularly limited, if it is a microarray carrying all yeast genes, and, for example, "GeneChip" manufactured by Affymetrix and "3D-Gene" manufactured by Toray Industries Inc. can be used favorably. It is more preferably "3D-Gene."

Here, when the fluorescence intensity of all genes is determined by using the DNA microarray, a gene showing a fluorescence intensity larger by 5 times or more than the average will be defined as the "gene expressed in a gene expression amount larger by 5 times or more than the average relative expression amount of all genes." A gene showing a value larger by 7 times or more will be defined as the "gene expressed in a gene expression amount larger by 7 times or more than the average relative expression amount of all genes." Further, a gene showing a value larger by 10 times or more will be defined as the "gene expressed in a gene expression amount larger by 10 times or more than the average relative expression amount of all genes."

The promoter of a gene expressed in a gene expression amount larger by 5 times or more than the average relative expression amount of all genes after 50 hours from start of culture in continuous culture with simultaneous filtration of a yeast strain having a lactic acid-producing ability is the promoter of a gene that can be determined by DNA microarray measurement by sampling the yeast strain at a point after 50 hours form start of culture in continuous culture with simultaneous filtration of a yeast strain having a lactic acid-producing ability and using the total RNAs extracted from the yeast.

The "promoter" means a nucleotide sequence involved in initiation of transcription from gene to mRNA, and it normally indicates a sequence 5 terminal-sided upstream of the gene present on chromosome. The nucleotide sequence length of the promoter is preferably 1 to 3000 bp, more preferably 1 to 1000 bp, but it is not particularly limited, if it is a nucleotide sequence that can initiate transcription of its downstream gene into mRNA. The mutation and operation for improvement in transcription activity of the promoter are already known, and the promoters also include promoters modified by known methods.

Examples of the promoters for the gene expressed in a gene expression amount larger by 5 times or more, preferably 7 times or more and more preferably 10 times or more, than the average relative expression amount of all genes after 50 hours from start of culture in continuous culture with simultaneous filtration of a yeast strain having a lactic acid-producing ability are CDC19 (cell division cycle 19) gene, IPP1 (inorganic pyrophosphatase 1) gene, ARF1 (ADP-ribosylation factor 1) gene, CUPS gene, RPL28 (ribosomal protein L28) gene, TRX2 (thioredoxin 2) gene, HSP104 (heat shock protein 104) gene, AHP1 (alkyl hydroperoxide reductase 1) gene, YMR122 W-A, CIT1 (citrate synthase 1) gene, RPS15 (ribosomal protein S15) gene, ALD4 (aldehyde dehydrogenase 4) gene, YPL225W, HSP26 (heat shock protein 26) gene, PGK1 (phosphoglycerate kinase 1) gene, SED1 (suppression-of-exponential-defect 1) gene, MFA1 (mating factor 1) gene, HYP2 (hypusine-containing protein 2) gene, HSP12 (heat shock protein 12) gene, QCR6 (ubiquinol-cytochrome C reductase complex 6) gene, HXK1 (hexokinase 1) gene, TDH3 (glyceraldehyde-3-phosphate dehydrogenase 3) gene, ENOL (enolase 1) gene, BGL2 (β-glucanase 2) gene, YJL133C-A, QCR8 (ubiquinol cytochrome C reductase complex 8) gene, FBA1 (fructose-1,6-biphosphate aldolase 1) gene, CWP2 (cell wall-associated protein 2) gene, CCW12 (cell wall-associated protein 12) gene, TMA10 (translation machinery-associated 10) gene, SIP18 gene, HOR7 (high-osmotic pressure response 7) gene, CCW14 (cell wall-associated protein 14) gene, PIR3 (protein-containing internal repeat 13) gene, CYS3 (systathionase 3) gene, CDC48 (cell division cycle 48) gene, LYS20 (homocitrate synthase 20) gene, HSP31 (heat shock protein 31) gene, ARG5,6 (acetyl-glutamate kinase 5,6) genes, RPS24A (40S-ribosome protein S24) gene, RPL29 (ribosome protein L29) gene, RPL24 A (ribosome protein L24) gene, ADH4 (alcohol dehydrogenase 4) gene, MUP1 (methionine uptake 1) gene, RPL11B (ribosome protein L11B) gene, THI4 (thiamine biosynthesis 4 gene) gene, RPL24B (ribosome protein L24B) gene, RPS0A (40S ribosome protein SA) gene, RPL27A (ribosome-protein L27A) gene, RPL16 A (ribosome-protein L16A) gene, RPS21B (40S ribosome protein S21B) gene, RPS5 (40S ribosome protein S5) gene, HOME (homoserine dehydrogenase 6) gene, PDC5 (pyruvate decarboxylase 5) gene, THI7 (thiamine biosynthesis 7) gene, MET17 (cysteine synthase 17) gene, ECM40 (amino acid-N-acetyl transferase 40) gene, ARG1 (arginase 1) gene, ZPS1 (zinc-pH/regulated surface layer protein 1) gene and IDH2 (isocitrate dehydrogenase 2) genes, and particularly preferable are the promoters for SED1 gene, CWP2 gene and ENO1 gene.

More preferable are the promoters having a nucleotide sequence selected from the following sequences (a) to (c):
 (a) Promoters having a nucleotide sequence represented by the following SEQ ID Nos. 1 to 3;

(b) Promoters having a nucleotide sequence that can hybridize with a nucleotide sequence represented by the following SEQ ID Nos. 1 to 3 or a nucleotide sequence having part of it under stringent condition; and (c) Promoters having a nucleotide sequence obtained by deletion, substitution and/or addition of one or more bases from a nucleotide sequence selected from those represented by the following SEQ ID Nos. 1 to 3:

```
SEQ ID No. 1: (SED1 gene: derived from Saccharomyces cerevisiae)
aggattttaa tctgttggag ttaaggtgaa tacgttttc catattgggg tatgcagctc gaacctaaag tggtatgtac atcccctc aagcacaccc attacccta taggattaat gtaagcaaca gcttacacgg aattggaaat actattcaac gatccatgca tctgccagat tcggacatgc atattcccca attggatata gaaattaac gtaaggcagt atcttttcac aatgtacttg caacgcggcg acttaaagtt gaagtacaac ctgcagcagc ggcttttgt acggtacgcc aaactgtcaa tggataatat tgcgtagacc gaaaaaggta atcctcaaca ctacccgtgg tggatgacct aaagcagtaa tattggttgg aattatctcc cagacggcac cgtctcccg agaaagctta gccccgaggt ctaccttcca tacaccactg attgctccac gtcatgcggc cttctttcga ggacaaaaag gcatatatcg ctaaaattag ccatcagaac cgttattgtt attatatttt cattacgaaa gaggagaggg cccagcgcgc cagagcacac acggtcattg attacttat ttggctaaag atccatccct tctcgatgtc atctctttcc attcttgtgt atttttgatt gaaatgatt ttttgtccac taattctaa aaataagaca aaaagccttt aagcagtttt tcatccattt tactacggta aaatgaatta gtacggtatg gctcccagtc gcattatttt tagattggcc gtaggggctg gggtagaact agagtaagga acattgctct gccctcttt gaactgtcat ataaatacct gacctatttt attctccatt atcgtattat ctcacctctc tttttctatt ctcttgtaat tattgattta tagtcgtaac tacaaagaca agcaaaataa aatacgttcg ctctattaag SEQ ID No. 2: (CWP2 gene: derived from Saccharomyces cerevisiae)
ctaatagaca aggtgctatg agtgaattgc tagcctcccc ttttattt gtgcggtcac cgcaagggac aaagcttttc ttagaaaacc gtctgagaag cataacgtac gccatcccct agacatatta ataatgctac agatactatg ctgctcgtct ttttttgacg acccttttat tgcaatgtgc aactaatggc aaacaaccac atagtatcac agtattacat tgcctccacc gatgcggatg ttagggcgcc aagtctgtca tgaagcatgt tcctgtcata atcttgtatg caaaataccg cgttctgcgc cactgatatg ctaggcagca gcaacctatg cagaagattg cttttcccac gcctgtttta cgtctccagg gcacttgaaa caatgcagcg atcgccgcca caacacgcca aagagaagcg aaagtgggcc tgggcggcct cagtttcggc agaggtaaac aacacgaact gaactgcctt agctccgaag ggcaattcca caggcactcc gcggggcccg gccaaggccc aaaaggcgtg gaatatgcgc gttttgggc ataacaccc agtaccacgg ccggaacggg ccatataata agttttcac tctcaagaat ggtaaacgta aataggaaca tcccactacc ctagaaattg cggaaatttc gcgcttatca ttagaaaatc tggaaccgtc cttttcctc tttcttgcat ttccctttcc gtattattgc cattctttaa ctgcatttgg ggaaccgtag accaaagcc aaacagagaa atgtaacgtt ctaaaaaaa aacaacgaaa aaattgaaaa ataagataca ataatcgtat ataaatcagg cttcttgttc atcattttca attctcttct tgccatccct tttcctatct ttgttctttt cttctcataa tcaagaataa ataacttcat cacattcgct acacactaac aagaaaaaaa SEQ ID No. 3: (ENO1 gene: derived from Saccharomyces cerevisiae)
tagaaagcat actatactat tcgacacttc ctttcaatcc tggaattaac agtcacttt aaaaagaca tctaccgtga aggtgccgta gagtatcgcg ttaccatatc gccaaaaact
```

```
gatatacgcc gcggaaacca ggcaaacaat tgaaaagaaa aattttgagg aactctctgc atcgaagccg tctagagtta ccactagtca gatgccgcgg gcacttgagc acctcatgca cagcaataac acaacacaat ggttagtagc aacctgaatt cggtcattga tgcatgcatg tgccgtgaag cgggacaacc agaaaagtcg tctataaatg ccggcacgtg cgatcatcgt ggcggggttt taagagtgca tatcacaaat tgtcgcatta ccgcggaacc gccagatatt cattacttga cgcaaaagcg tttgaaataa tgacgaaaaa gaaggaagaa aaaaaaagaa aaataccgct tctaggcggg ttatctactg atccgagctt ccactaggat agcacccaaa cacctgcata tttggacgac ctttacttac accaccaaaa accactttcg cctctcccgc ccctgataac gtccactaat tgagcgatta cctgagcggt cctctttgt ttgcagcatg agacttgcat actgcaaatc gtaagtagca acgtctcaag gtcaaaactg tatggaaacc ttgtcacctc acttaattct agctagccta ccctgcaagt caagaggtct ccgtgattcc tagccacctc aaggtatgcc tctccccgga aactgtggcc ttttctggca cacatgatct ccacgatttc aacatataaa tagcttttga taatggcaat attaatcaaa tttattttac ttctttcttg taacatctct cttgtaatcc cttattcctt ctagctattt ttcataaaaa accaagcaac tgcttatcaa cacacaaaca ctaaatcaaa
```

The "stringent condition" is a condition in which a probe hybridizes to its target sequence at a degree higher than that to other sequences (e.g., at least twice larger than the background). The stringent condition depends on the sequence and varies according to the environment in which hybridization is carried out. Here, the stringent condition is a hybridization temperature of 37° C. in the presence of 50% formamide, and a more severe condition is a temperature of approximately 42° C. A further stringent condition is a hybridization temperature of approximately 65° C. in the presence of formamide.

We provide a lactate dehydrogenase-expressing cassette containing one of the promoters described above.

We also provide a lactate dehydrogenase-expressing cassette containing a promoter selected from the following group (a) and a lactate dehydrogenase-coding gene selected from the group (b):

(a)
(1) Promoters having a nucleotide sequence represented by any one of SEQ ID Nos. 1 to 3;
(2) Promoters having a nucleotide sequence that hybridizes with a nucleotide sequence represented by any one of SEQ ID Nos. 1 to 3 or a nucleotide sequence having part of it under stringent condition; and
(3) Promoters having a nucleotide sequence obtained by deletion, substitution and/or addition of one or more bases from the nucleotide sequence represented by any one of the following SEQ ID Nos. 1 to 3; and (b)
(1) Genes coding lactate dehydrogenase having a nucleotide sequence represented by any one of the following SEQ ID Nos. 4 to 6;
(2) Genes coding lactate dehydrogenase having a nucleotide sequence that hybridizes with a nucleotide sequence represented by any one of the following SEQ ID Nos. 4 to 6 or a nucleotide sequence having part of it under stringent condition; and
(3) Genes coding lactate dehydrogenase having a nucleotide sequence obtained by deletion, substitution and/or addition of one or more bases in the nucleotide sequences represented by any one of the following SEQ ID Nos. 4 to 6:

```
SEQ ID No. 4: derived from Xenopus laevis
atggcaactg tgaaggataa actcatccac aatgtggtca aggaggagtc gctcccccag aacaaggtca ccattgtggg tgtgggggcc gtgggcatgg cctgtgccat cagtgtcctg cagaaggatt tggcagatga gcttgcactt gttgatgtga tagaagacaa actgaagggg gaaatgatgg atctccagca tggcagtctg ttccttcgta cccccaagat tgtctcaggg aaagattaca gcgtcactgc aaactccaag ctggtagttg tgacggccgg ggcccgtcag caggagggag agagtcgcct gaatctggtt cagcgcaatg tcaacatctt caaattcatc attcccaaca ttgtcaagta cagccccaac tgcaccctgc tcatcgtctc caacccagtg gacattctga catatgtggc ctggaagatc agtggattcc ccaaaaaccg tgtcattggc agcggctgca atttggactc tgcccgtttc cgttacctca tgggggcagaa gtttgggatc cacacccaga gctgccacgg ttgggtcatt ggggaacacg gagactcgag tgtgccagtg tggagtgggg tgaatgtggc tggcgtgtcc ctgaaaaccc tgcaccccga tattgggagt
```

```
gacgcagaca aggagaactg gaaggaggtg cacaagcagg ttgtggacag cgcctatgaa gtgatcaagc tgaagggcta cacctcctgg gctattggcc tgtccgtagc tgacctgtct gagagtatcc tgaagaacct ccgccgagtc catcccattt ccacaatggt caagggcatg tacggcgtga ataatgatgt tttcctcagt gtccoctgtg tgttgggcaa cttgggcatc acagacgtgg ttaacatgac gctgaaggca gatgaagagg atcgcttacg caagagcgca gacaccctgt gggccatcca aaggagctg cagttctag
```

SEQ ID No. 5: derived from *Homo sapiens*
```
atggcaactc taaaggatca gctgatttat aatcttctaa aggaagaaca gacccccag aataagatta cagttgttgg ggttggtgct gttggcatgg cctgtgccat cagtatctta atgaaggact tggcagatga acttgctctt gttgatgtca tcgaagacaa attgaaggga gagatgatgg atctccaaca tggcagcctt ttccttagaa caccaaagat tgtctctggc aaagactata atgtaactgc aaactccaag ctggtcatta tcacggctgg ggcacgtcag caagagggag aaagccgtct taatttggtc cagcgtaacg tgaacatatt taaattcatc attcctaatg ttgtaaaata cagcccgaac tgcaagttgc ttattgtttc aaatccagtg gatatcttga cctacgtggc ttggaagata agtggttttc ccaaaaaccg tgttattgga agtggttgca atctggattc agcccgattc cgttacctga tgggggaaag gctgggagtt cacccattaa gctgtcatgg gtgggtcctt ggggaacatg gagattccag tgtgcctgta tggagtggaa tgaatgttgc tggtgtctct ctgaagactc tgcacccaga tttagggact gataaagata aggaacagtg gaagagggtt cacaagcagg tggttgagag tgcttatgag gtgatcaaac tcaaaggcta cacatcctgg gctattggac tctctgtagc agatttggca gagagtataa tgaagaatct taggcgggtg cacccagttt ccaccatgat taagggtctt tacggaataa aggatgatgt cttccttagt gttccttgca ttttgggaca gaatggaatc tcagaccttg tgaaggtgac tctgacttct gaggaagagg cccgtttgaa gaagagtgca gatacacttt gggggatcca aaaggagctg caatttta
```

SEQ ID No. 6: derived from *Leuconostoc mesenteroides*
```
atgaagattt ttgcttacgg cattcgtgat gatgaaaagc catcacttga gaatggaaa gcggctaacc cagagattga gtggactac acacaagaat tattgacacc tgaaacagct aagttggctg agggatcaga ttcagctgtt gtttatcaac aattggacta tacacgtgaa acattgacag ctttagctaa cgttggtgtt actaacttgt cattgcgtaa cgttggtaca gataacattg attttgatgc agcacgtgaa tttaacttta acatttcaaa tgttcctgtt tattcaccaa atgctattgc agaacactca atgcttcaat tatctcgttt gctacgtcgc acgaaagcat tggatgccaa aattgctaag cgagacttgc gttgggcacc aacaactgga cgtgaaatgc gtatgcaaac agttggtgtt attggtacag tcatattgg ccgtgttgct attaacattt tgaaaggctt tggggccaag gttattgctt atgacaagta cccaaatgct gaattacaag cagaaggttt gtacgttgac acattagacg aattatatgc acaagctgat gcaatttcat tgtatgttcc tggtgtacct gaaaaccatc atctaatcaa tgcagatgct attgctaaga tgaaggatgg tgtggttatc atgaacgctc gcgtggtaa tttgatggac attgacgcta ttattgatgg tttgaattct ggtaagattt cagacttcgg tatggacgtt tatgaaaatg aagttgcttg ttcaatgaag attggtctgg taagaattc cccagatgct aagattgctg acttgattgc acgcgaaaat gttatgatca ccccacacac ggctttctat acaactaaag ctgttctaga aatggttcac caatcatttg atgcagcagt tgctttcgcc aagggtgaga agccagctat tgctgttgaa tattaa
```

Transformant Yeast Strain

We provide a transformant yeast strain having at least one lactate dehydrogenase-expressing cassette in chromosome. The transformant yeast strain can gave the lactate dehydrogenase-expressing cassette introduced at any position of the chromosome where the LDH can be expressed from the lactate dehydrogenase-expressing cassette. Preferably, it is a yeast in which at least one gene selected from SED1 gene, CWP2 gene and EN01 gene is substituted by the lactate dehydrogenase-expressing cassette.

The yeast can be used favorably, if it is a yeast into which the lactate dehydrogenase-expressing cassette can be introduced. An example thereof is a yeast belonging to *Saccharomyces* species, *Schizosaccharomyces* species, *Zygosaccharomyces* species, *Kluyveromyces* species or *Candida* species. It is preferably a yeast belonging to *Saccharomyces* species. It is more preferably *Saccharomyces cerevisiae.*

Production Method of Lactic Acid

We provide a method of producing lactic acid, comprising culturing the transformant yeast strain. The culture used may be batch culture, feeding culture (fed batch culture), chemostat culture or continuous culture. It is preferably continuous culture. It is more preferably continuous culture of filtering the culture solution through a separation membrane, recovering lactic acid from the filtrate, holding or feeding back the unfiltered solution to the culture solution and replenishing the medium to the culture solution.

Raw fermentation materials for the yeast are not particularly limited, if they accelerate growth of the yeast in fermentation culture and the desirable fermentation product lactic acid is produced efficiently. A favorable fermentation raw material is a liquid medium containing carbon sources, nitrogen sources, inorganic salts and, as needed, amino acids and organic trace nutrients such as vitamins in suitable amounts.

Examples of the carbon sources for use include sugars such as glucose, sucrose, fructose, galactose and lactose; mixtures containing these sugars such as starch hydrolysate, sweet potato syrup, sugar beet syrup, Hi Test molasses and sugarcane extract; organic acids such as acetic acid and fumaric acid; alcohols such as ethanol; glycerol; and the like. The sugars above are carbohydrates having an aldehyde group or a ketone group, which are the first oxidation products of polyvalent alcohols, and they are grouped into aldoses having aldehyde groups and ketoses having ketone groups.

Examples of the nitrogen sources include ammonia gas, ammonia water, ammonium salts, urea, nitrate salts, other organic nitrogen sources used auxiliary (such as oil cakes, soy bean hydrolysate, casein decomposition products, other amino acids, vitamins, cone steep liquor, yeast or yeast extract, fillet extracts, peptides such as peptone, various fermentation microbes and the hydrolysates thereof) and the like.

Examples of the inorganic salts added as needed include phosphate salts, magnesium salts, calcium salts, iron salts, manganese salts and the like.

When a particular nutrient is needed for growth of the yeast, the nutrient can be added as a standard reagent or a natural product containing the same. In addition, an antifoam may be added as needed.

The fermentation culture solution means a solution obtained after growth of the yeast strain with the fermentation raw materials. The composition of the fermentation raw materials to be added may be altered properly according to the composition of the fermentation raw materials used when the culture is initiated. If the composition of the fermentation raw materials added is different from that of the fermentation raw material added at first, modification leading to increase in productivity of desirable lactic acid is preferable. It is often possible to decrease the production cost of lactic acid, that is, to increase the productivity of lactic acid in the broad sense, for example by decreasing the percentages by weight of the nitrogen source, inorganic salts, amino acids and organic trace amount nutrients such as vitamins with respect to the carbon source. On the other hand, it may be possible to improve the productivity of lactic acid, by increasing the percentage by weight of nitrogen source, inorganic salts, amino acids and organic trace-amount nutrients such as vitamins with respect to the carbon source.

The concentrations of fermentation raw materials such as sugar in the fermentation culture solution are preferably kept at 5 g/L or less. The concentrations are kept more preferably at 3 g/L or less, more preferably at 1 g/L or less. It is aimed at minimizing the loss of the fermentation raw materials by withdrawal of the fermentation culture solution. Thus, the concentrations of the fermentation raw materials in the fermentation culture solution are desirably as low as possible.

Fermentation culture of yeast is normally, frequently carried out at a pH of 3 to 8 and a temperature in the range of 20 to 40° C. Because the product lactic acid is an acidic substance, the pH of the fermentation culture solution is adjusted to a predetermined value in the range above with an alkaline substance, urea, calcium carbonate, ammonia gas or the like.

If the oxygen-supplying rate is desirably increased in the yeast fermentation culture, it may be possible to increase the oxygen-supplying rate for example, by means of keeping the oxygen concentration at 21% or more by adding oxygen into air, pressurizing the fermentation culture solution, raising the agitation velocity or raising the ventilation rate. Alternatively if the oxygen-supplying rate is needed to be reduced, it may be also possible to mix air with an oxygen-free gas such as carbon dioxide, nitrogen or argon and supply the mixed gas.

Continuous culture (withdrawal) may be initiated after the yeast concentration is increased by batch culture or fed batch culture in the early phase of culture, or alternatively, continuous culture may be started simultaneously with culture by seeding yeast at higher concentration. It is possible to supply the fermentation raw material solution and withdraw the cultured solution simultaneously from a suitable point. The supply of the fermentation raw material and the withdrawal of the cultured solution may not be carried out at the same time. Alternatively, the supply of the fermentation raw material and the withdrawal of the cultured solution may be carried out continuously or intermittently. The aforedescribed nutrients needed for growth of the microbes are preferably added to the fermentation raw material solution for continuous growth of the microbes.

For more effective production, the concentration of the yeast in the fermentation culture solution is preferably kept high in the range in which the environment of the fermentation culture solution is not inadequate for growth of the yeast and the death rate is not increased. It is possible, for example, to obtain more favorable productivity by keeping the yeast concentration, as dry weight, at 5 g/L or more. The maximum concentration of the yeast is not particularly limited, if it does not cause troubles in operation of the continuous fermentation apparatus or lead to deterioration in productivity.

When continuous culture is carried out by using fresh microbes capable of fermentation production, it is preferably, normally carried out in a single fermentation reaction tank for control of culture. However, in the case of a continuous culture method of producing lactic acid with simultaneous growth of microbes, the number of the fermentation reaction tanks is arbitrary. Multiple fermentation reaction tanks may be used, for example because the capacity of a fermentation reaction tank is small. It is possible in such a case to obtain the fermentation product at high productivity, even if the continuous culture is carried out, as the multiple fermentation reaction tanks are connected in parallel or in series to each other by pipings.

Lactic acid contained in the culture solution produced by the method of producing lactic acid may be separated and purified by combination of known methods such as ion exchanging, concentration, distillation and crystallization.

For example, a fermentation apparatus used in the method of producing lactic acid is configured to have mainly a fermentation reaction tank for production of lactic acid, holding the transformant yeast strain therein, and a separation membrane element containing a porous membrane for separation of the culture solution from the transformant yeast strain by filtration. The separation membrane element may be installed inside or outside the fermentation reaction tank.

In the method of producing lactic acid by continuous culture by means of filtering the culture solution with a separation membrane, recovering lactic acid from the filtrate, holding or feeding back the unfiltered solution to the culture solution and adding the medium to the culture solution, it is preferable to use a porous membrane having an average micropore diameter of 0.01 µm or more and less than 1 µm as the separation membrane and to filtrate the culture solution at a filtration pressure, i.e., transmembrane pressure difference, in the range of 0.1 to 20 kPa. Because it is not particularly necessary to pressurize the fermentation reaction tank, a driving means for circulation of the fermentation culture solution between the filtration separation apparatus and the fermentation reaction tank is not needed, and thus, the separation membrane element can be installed in the fermentation reaction tank for reduction in size of the fermentation culture apparatus.

The configuration of the porous membrane favorably used as the separation membrane will be described below. The porous membrane is a membrane having a suitable separability and water permeability according to the quality and application of the treated water, and it is preferably a porous membrane having a porous resin layer, from the points of separation properties such as blocking performance, water permeability and staining resistance. Such a porous membrane has a porous resin layer functioning as a functional separation layer on the surface of the porous base material. The porous base material strengthens the separation membrane by supporting the porous resin layer.

The material for the porous base material is not particularly limited and may be an organic or inorganic material, but an organic fiber is used favorably. Examples of favorable porous base materials include woven and nonwoven fabrics produced by using an organic fiber such as cellulosic fiber, cellulose triacetate fiber, polyester fiber, polypropylene fiber or polyethylene fiber, and, among the materials above, nonwoven fabrics, which are cheap, produced easily and allow relatively easier control of density, are used favorably.

The porous resin layer functions as a functional separation layer, as described above, and an organic polymer membrane may be used favorably. Examples of the materials for the organic polymer membrane include polyethylene resins, polypropylene resins, polyvinyl chloride resins, polyvinylidene fluoride resins, polysulfone resins, polyether sulfone resins, polyacrylonitrile resins, cellulosic resins, cellulose triacetate resins and the like. The organic polymer membrane may be a mixture of resins containing the resin as principal component. The term "principal component," as used herein, means that the component is contained in an amount of 50 wt % or more, preferably 60 wt % or more. In particular, the raw material constituting the porous resin layer is preferably a resin allowing easy membrane formation as its solution that is superior in physical durability and chemical resistance, such as polyvinyl chloride resin, polyvinylidene fluoride resin, polysulfone resin, polyether sulfone resin or polyacrylonitrile resin, and a polyvinylidene fluoride resin or a resin containing it as the principal component is used most favorably.

The polyvinylidene fluoride resin favorably used is a homopolymer of vinylidene fluoride, but copolymers thereof with a vinyl monomer copolymerizable with vinylidene fluoride are also used favorably. Examples of the vinyl monomers copolymerizable with vinylidene fluoride include tetrafluoroethylene, hexafluoropropylene, ethylene trichloride fluoride, and the like.

The separation membrane may be a flat membrane or a hollow fiber membrane. In the case of a flat membrane, the average thickness is determined according to applications selection, but preferably selected in the range of 20 µm or more and 5000 µm or less, more preferably 50 µm or more and 2000 µm or less.

As described above, the separation membrane is preferably a porous membrane made of a porous base material and a porous resin layer. The porous resin layer may or may not be penetrated into the porous base material then, and the degree is selected according to application. The average thickness of the porous base material is preferably selected in the range of 50 µm or more and 3000 µm or less. When the porous membrane is a hollow fiber membrane, the internal diameter of the hollow fiber is preferably selected in the range of 200 µm or more and 5000 µm or less, and the film thickness is preferably selected in the range of 20 µm or more and 2000 µm or less. The hollow fiber may contain a tubular woven or knitted fabric of organic or inorganic fiber therein.

First, a method of producing a flat membrane, among the porous membranes above, will be described briefly.

A film of a concentrated solution containing the resin and a solvent is formed on the surface of a porous base material, while impregnation of the concentrated solution into the porous base material is permitted. Subsequently, only the film-sided surface of the film-carrying porous base material is brought into contact with a coagulation bath containing a nonsolvent, for solidification of the resin and formation of a porous resin layer on the surface of the porous base material. The concentrated solution is prepared by dissolving a resin in solvent. The concentrated solution may contain a nonsolvent additionally. The temperature of the concentrated solution is preferably selected normally in the range of 15 to 120° C., from the viewpoint of membrane-forming efficiency.

The concentrated solution may then contain a pore-forming agent additionally. The pore-forming agent has an action to make the resin layer porous, as it is extracted from the coated film when it is immersed in the coagulation bath. It may control the size of the average micropore diameter, by addition of the pore-forming agent. The pore-forming agent is preferably highly soluble in the coagulation bath. Examples of the pore-forming agents favorably used include inorganic salts such as calcium chloride and calcium carbonate. Alternatively, a polyoxyalkylene such as polyethylene glycol and polypropylene glycol; a water-soluble polymer compound such as polyvinylalcohol, polyvinylbutyral and polyacrylic acid; and glycerol may be used as the pore-forming agent.

The solvent is a compound dissolving resins. The solvent accelerates formation of the porous resin layer in interaction with the resin and the pore-forming agent. Examples of the solvents for use include N-methylpyrrolidinone (NMP), N,N-dimethylacetamide (DMAc), N,N-dimethylformamide (DMF), dimethylsulfoxide (DMSO), N-methyl-2-pyrrolidone, methylethyl-ketone, tetrahydrofuran, tetramethylurea, trimethyl phosphate, cyclohexanone, isophorone, γ-butylolactone, methylisoamylketone, dimethyl phthalate, propylene glycol methylether, propylene carbonate, diacetone alcohol, glycerol triacetate, acetone, methylethylketone and the like. Among them, solvents in which the resin is highly soluble, such as NMP, DMAc, DMF and DMSO, are used favorably. These solvents may be used alone or as a mixture of two or more. The concentrated solution may be prepared by dissolving the aforedescribed resin in the solvent described above, preferably at a concentration of 5 wt % or more and 60 wt % or less.

For example, components other than solvents such as polyethylene glycol, polyvinyl-alcohol, polyvinylpyrrolidone and glycerol may be added to the solvent. The nonsolvent is a liquid not dissolving resins. The nonsolvent controls the speed of resin solidification and thus the size of the micropore. Water or an alcohol such as methanol or ethanol may be used as the nonsolvent. In particular, water and methanol are preferable from the point of price. The nonsolvent may be a mixture of these solvents.

Hereinafter, the method of producing a hollow fiber membrane, among the porous membranes, will be described briefly.

The hollow fiber membrane may be prepared by extruding a concentrated solution containing a resin and a solvent out of the external pipe of a double-pipe die and a hollow-forming fluid out of the internal pipe of the double-pipe die and solidifying the solution by cooling in a cooling bath.

The concentrated solution may be prepared by dissolving the resin described in the method of producing a flat membrane in the solvent described in the method of producing a flat membrane preferably at a concentration of 20 wt % or more 60 wt % or less. The hollow-forming fluid for use is normally gas or liquid. In addition, an additional porous resin layer may be coated (laminated) on the outermost surface of the hollow fiber membrane obtained. The lamination may be performed, for example, for modification of the properties of the hollow fiber membrane, such as hydrophilicity-hydrophobic and micropore diameter to desired properties. The additional porous resin layer laminated may be prepared by bringing the concentrated solution containing a resin dissolved in a solvent into contact with a coagulation bath containing a nonsolvent and thus solidifying the resin. For example, materials similar to those for the organic polymer membrane described above may be used favorably as the resin materials. As for the lamination method, the hollow fiber membrane may be immersed into the concentrated solution or the concentrated solution be applied on the surface of the hollow fiber membrane, and the lamination amount may be adjusted after lamination by squeezing out part of the concentrated solution adhered or blowing out the concentrated solution with an air knife.

The separation membrane gives a separation membrane element in combination with a supporting member. A separation membrane element having a supporting plate used as the supporting member and a separation membrane formed at least on one face of the supporting plate is a favorable aspect of the separation membrane element having the separation membrane. If it is difficult to increase the membrane area in the shape, it is preferable to form a separation membrane on both faces of the supporting plate for increase of water permeability.

When the porous membrane used as separation membrane has an average micropore diameter in the range of 0.01 μm or more and less than 1 μm, as described above, the membrane shows both high exclusion rate prohibiting leakage of microbes and sludge and high water permeability at the same time, and it may retain favorable water permeability without clogging for an extended period of time at higher accuracy and reproducibility. If microbes are used, the average micropore diameter of the porous membrane is preferably 0.4 μm or less, and the membrane can be used more favorably, if its average micropore diameter is less than 0.2 μm. The water permeability may decrease when the average micropore diameter is excessively smaller and, thus, the average micropore diameter is 0.01 μm or more, preferably 0.02 μm or more and still more preferably 0.04 μm or more.

The average micropore diameter may be determined by measuring the diameters of all micropores observable in the range of 9.2 μm×10.4 μm by observation under scanning electron microscope at a magnification of 10,000 times and averaging the diameters thus obtained.

The standard deviation σ of the average micropore diameter is preferably 0.1 μm or less. In addition, it may obtain homogeneous permeate, when the standard deviation of the average micropore diameter is small, i.e., when the micropore diameter is uniform in size. The standard deviation of the average micropore diameter is desirably smaller as much as possible, because it is easier to control the fermentation operation.

When the number of micropores observed in the range of 9.2 μm×10.4 μm described above is designated as N, each diameter measured as Xk and the average of the micropore diameter as X(ave), the standard deviation ρ of the average micropore diameter is calculated according to the following Formula 1:

Formula 1

$$\sigma = \sqrt{\frac{\sum_{k=1}^{N}(X_k - X(ave))^2}{N}}$$ (Formula 1)

Permeability of the fermentation culture solution is one of the important properties of the separation membrane, and pure water permeability coefficient of the separation membrane before use may be used as the indicator of permeability. The pure water permeability coefficient of the separation membrane, as determined by using water purified by reverse osmosis membrane at a temperature of 25° C. and a head height of 1 m, is preferably $2\times10^{-9}$ m$^3$/(m$^2$·s·Pa). It may obtain practically sufficient water permeability, when the pure water permeability coefficient is $2\times10^{-9}$ m$^3$/(m$^2$·s·Pa) or more and $6\times10^{-7}$ m$^3$/(m$^2$·s·Pa) or less. More preferable, the pure water permeability coefficient is $2\times10^{-9}$ m$^3$/(m$^2$·s·Pa) or more and $1\times10^{-7}$ m$^3$/(m$^2$·s·Pa) or less.

The membrane surface roughness of the separation membrane is a factor exerting an influence on clogging of the separation membrane. It may decrease the exfoliation coefficient and the film resistance of the separation membrane favorably and carry out continuous fermentation at lower transmembrane pressure difference, when the membrane surface roughness is preferably 0.1 μm or less. It thus leads to prevention of clogging and stabilized continuous fermentation, and for that reason, the surface roughness is preferable lower as much as possible.

In addition, it would be possible, by reducing the membrane surface roughness of the separation membrane, to reduce the shearing force generated on the membrane surface during filtration of microbes, thus leading to suppression of decomposition of the microbes and clogging of the separation membrane, and to continue stabilized filtration for an extended period of time.

The membrane surface roughness may be determined by using the following atomic force microscope apparatus (AFM) and the following apparatus under the condition below. The atomic force microscope apparatus (AFM) used is not particularly limited, if it is an apparatus equivalent to or higher than the following apparatus in grade.

Apparatus: atomic force microscope apparatus (Nanoscope IIIa, manufactured by Digital Instruments Co., Ltd.)
Condition: Probe: SiN cantilever (manufactured by Digital Instruments Co., Ltd.))
: Scan mode: contact mode (gas-phase measurement) underwater tapping mode (underwater measurement)
: Scanning range: 10 μm, 25 μm square (gas-phase measurement) 5 μm, 10 μm square (underwater measurement)
: Scanning definition: 512×512
Sample preparation:
In measurement, the membrane sample was immersed in ethanol at room temperature for 15 minutes and then in RO water for 24 hours and then dried in air before use. The RO water is water, from which impurities such as ions and salts are removed by filtration with a reverse osmosis membrane (RO membrane), a kind of filtration membrane. The size of the pores in the RO membrane is approximately 2 nm or less.

The membrane surface roughness ($d_{rough}$) is calculated from the height of each point in the Z axis direction observed under the AFM according to the following Formula 2:

Formula 2

$$d_{rough} = \sum_{n=1}^{N} \frac{|Z_n - \overline{Z}|}{N}$$ (Formula 2)

$D_{rough}$: Surface roughness (μm)
$Z_n$: Height in Z axis (μm)
$\overline{Z}$: Average height in the scanning range (μm)
N: Number of measured samples The transmembrane pressure difference when microbes are filtered through the separation membrane is not particularly limited, if it is a condition preventing facile clogging by the microbes and the medium components, but it is important to perform the filtration treatment at a transmembrane pressure difference in the range of 0.1 kPa or more and 20 kPa or less. The transmembrane pressure difference is preferably in the range of 0.1 kPa or more and 10 kPa or less, more preferably in the range of 0.1 kPa or more and 5 kPa. Deviation form the range of the transmembrane pressure difference may result in rapid clogging by the microbes and the medium components, possibly leading to decrease of the amount of permeate water and troubles in continuous fermentation operation.

As for the driving force for filtration, the transmembrane pressure difference may be generated in the separation membrane by the principle of siphon of using the difference in liquid level (head difference) between the fermentation culture solution and the separated membrane-treated water. For filtration-driving force, a suction pump may be installed to the side of separated membrane-treated water or a pressurization pump may be installed to the fermentation culture solution side of the separation membrane. The transmembrane pressure difference may be controlled by modifying the difference in liquid level between the fermentation culture solution and the separated membrane-treated water. When a pump is used for generation of transmembrane pressure difference, the transmembrane pressure difference may be controlled by the suction pressure force and the transmembrane pressure difference may be controlled by the gas or liquid pressure for pressurization of the fermentation culture solution side. If such pressure control is needed, it is possible to control the transmembrane pressure difference, by using the pressure difference between the pressure of the fermentation culture solution side and the pressure of the separated membrane-treated water side as the transmembrane pressure difference.

In addition, the separation membrane preferably shows performance allowing filtration treatment at a transmembrane pressure difference during filtration treatment in the range of 0.1 kPa or more and 20 kPa or less. As described above, the separation membrane preferably has a pure water permeability coefficient before use, as calculated from the water permeability that is determined by using reverse osmosis membrane-purified water at a temperature of 25° C. and at a head height of 1 m, preferably in the range of $2 \times 10^{-9}$ m$^3$/(m$^2$·s·Pa) or more, more preferably in the range of $2 \times 10^{-9}$ m$^3$/(m$^2$·s·Pa) or more and $6 \times 10^{-7}$ m$^3$/(m$^2$·s·Pa) or less.

A typical example of the continuous fermentation apparatus used in the method of producing lactic acid, in which a separation membrane element is installed in the fermentation reaction tank, is shown in FIG. 1. FIG. 1 is a schematic side view explaining the aspect of the membrane-separation continuous fermentation apparatus. In FIG. 1, the membrane-separation continuous fermentation apparatus essentially has a fermentation reaction tank 1 for fermentation culture of yeast and a head-difference control unit 3 for control of the amount of the fermentation culture solution in the fermentation reaction tank 1. A separation membrane element 2 is installed in the fermentation reaction tank 1 and the separation membrane element 2 has a porous membrane incorporated therein. Examples of the porous membranes for use include the separation membrane and the separation membrane element disclosed in WO 2002/064240 pamphlet.

Hereinafter, favorable aspects of the continuous fermentation by the membrane-separation continuous fermentation apparatus shown in FIG. 1 will be described. The medium is fed into the fermentation reaction tank 1 continuously or intermittently by a medium-supplying pump 7. The medium may be disinfected as needed by heating sterilization, heating disinfection or filter sterilization treatment before supply into the fermentation reaction tank 1. During fermentation production, the fermentation solution in the fermentation reaction tank 1 may be agitated as needed by a stirrer 5 in fermentation reaction tank 1. A desired gas may be supplied, as needed, into the fermentation reaction tank 1 by a gas-supplying apparatus 4. The gas supplied then may be recovered and recycled back into the gas-supplying apparatus 4. In addition, the pH of the fermentation solution in the fermentation reaction tank 1 may be adjusted, as needed, by a pH sensor-control unit 9 and a pH-adjusted solution supply pump 8. High-productivity fermentation production may also be conducted by regulating, as needed, the temperature of the fermentation culture solution in the fermentation reaction tank 1 by a temperature controller 10.

Regulation of pH and temperature was exemplified here for regulation of the physical and chemical conditions of the fermentation culture solution by the instrumentation-control unit, but the regulation may also be made, as needed, by a measurement of dissolved oxygen or ORP (oxidation-reduction potential), and the physical and chemical conditions may be regulated by using lactic acid concentration in the fermentation culture solution, as determined by an analyzer such as online chemical sensor, as an indicator. The method of supplying the medium continuously or intermittently is not particularly limited, but the amount and velocity of supplying the medium may be regulated properly by using the measure values of physical and chemical environments of the fermentation culture solution obtained by the instrumentation apparatus.

The fermentation culture solution are filtered and separated into yeast and fermentation products by the separation membrane element 2 installed in the fermentation reaction tank 1 and the fermentation products are discharged from the apparatus system. The filtered and separated yeast remains in the apparatus system, as the yeast concentration in the apparatus system is kept higher, thus permitting high-productivity fermentation production. The filtration and separation by the separation membrane element 2 is carried out, as driven by the head pressure difference with the water surface in the fermentation reaction tank 1, and does not demand an additional special driving force. The filtration-separation speed of the separation membrane element 2 and the amount of the fermentation solution in the fermentation reaction tank 1 may be regulated, as needed, properly with a level sensor 6 and a head pressure difference control unit 3. Although filtration and separation by separation membrane element 2 performed by head pressure difference was shown as the aspect above, the filtration and separation may be performed, as needed, by a pump or by suction filtration for example by gas or liquid or pressurization of the apparatus system.

Figure 2:
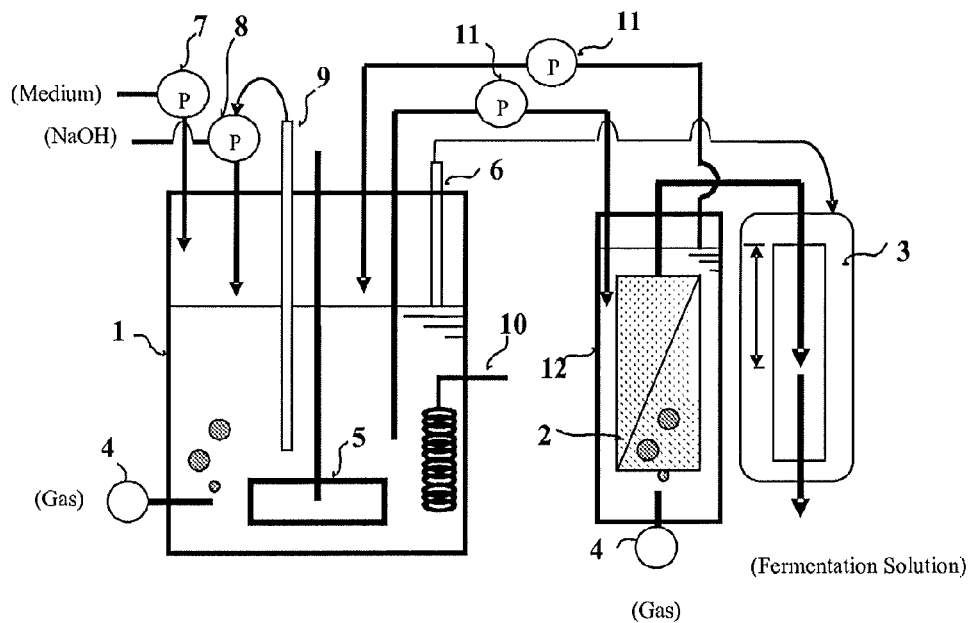
FIG. 2 is a schematic side view explaining another continuous fermentation apparatus for use in another membrane-separation.

Hereinafter, a typical example of the fermentation apparatuses used in the method of producing lactic acid, in which the separation membrane element is installed outside the fermentation reaction tank, is shown in the schematic view of FIG. 2. In FIG. 2 is a schematic side view explaining another aspect of the membrane-separation continuous fermentation apparatus.

In FIG. 2, the membrane-separation continuous fermentation apparatus essentially has a fermentation reaction tank 1 for fermentation culture of yeast, a membrane separation tank 12 having a separation membrane element 2 therein that is connected to the fermentation reaction tank 1 via a fermentation culture solution-circulating pump 11 and a head-difference control unit 3 for regulation of the amount of the fermentation culture solution in the fermentation reaction tank 1. The separation membrane element 2 has a porous membrane incorporated therein. Examples of the porous membranes for use include the separation membrane and the separation membrane element disclosed in WO 2002/064240 pamphlet.

In FIG. 2, the medium may be fed into the fermentation reaction tank 1 by a medium-supplying pump 7 and the fermentation culture solution in the fermentation reaction tank 1 may be agitated, as needed, with a stirrer 5. A desired gas may also be fed therein, as needed, by a gas-supplying apparatus 4. The gas supplied may then be recovered and recycled back into the gas-supplying apparatus 4. The pH of the fermentation culture solution may be adjusted, as needed, with a pH sensor-control unit 9 and a pH-adjusted solution supply pump 8. In addition, the temperature of the fermentation culture solution may be adjusted, as needed, by a temperature controller 10 for high-productivity fermentation production. Further, the fermentation culture solution in the apparatus is circulated between the fermentation reaction tank 1 and the membrane separation tank 12 by a fermentation culture solution-circulating pump 11. The fermentation culture solution containing the fermentation products is filtered and separated into yeast and fermentation products by the separation membrane element 2 and thus, the fermentation product lactic acid may be discharged out of the apparatus system.

The filtered and separated yeast remains in the apparatus system, as the yeast concentration in the apparatus system is kept higher, thus permitting high-productivity fermentation production. The filtration and separation by the separation membrane element 2 may be carried out by the head pressure difference from the water surface of the membrane separation tank 12 and does not demand an additional special power. The filtration-separation speed of the separation membrane element 2 and the amount of the fermentation culture solution in the apparatus system may be regulated, as needed, properly by a level sensor 6 and a head pressure difference control unit 3. A desired gas may be supplied, as needed, into the membrane separation tank 12 by the gas-supplying apparatus 4.

Although filtration and separation by separation membrane element 2 performed by head pressure difference was shown as the aspect above, the filtration and separation may be performed, as needed, by a pump or by suction filtration for example by gas or liquid or pressurization of the apparatus system. The transmembrane pressure difference may be adjusted and controlled by the means above.

Figure 3:
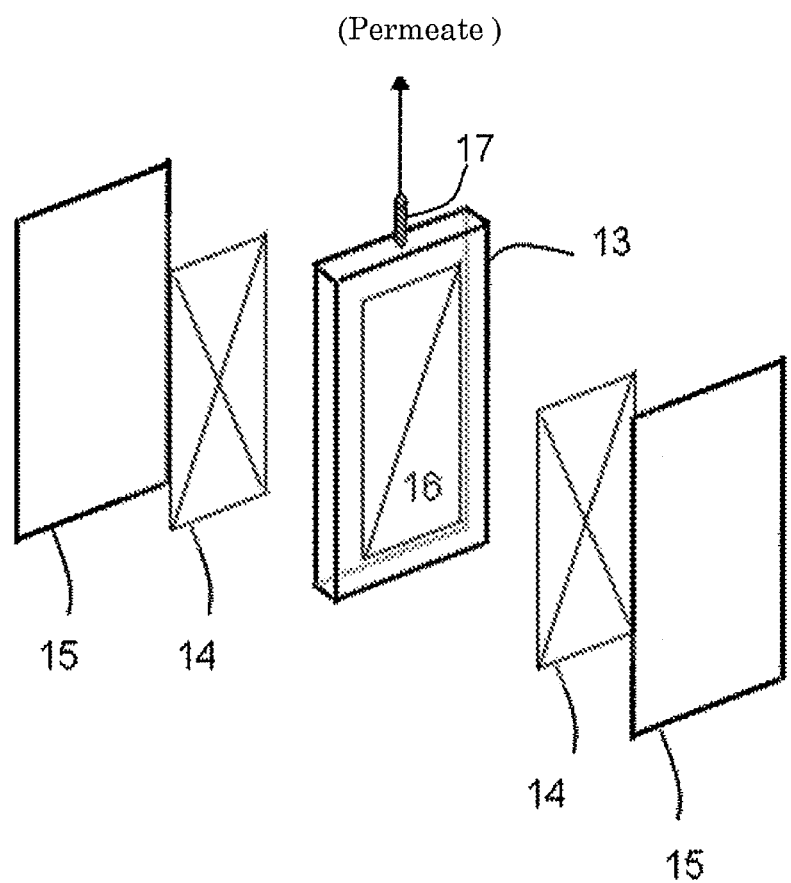
FIG. 3 is a schematic perspective view explaining the separation membrane element.

Hereinafter, the separation membrane and the separation membrane element disclosed in WO 2002/064240 pamphlet, a favorable separation membrane element, will be described briefly with reference to a drawing. FIG. 3 is schematic perspective view explaining an aspect of the separation membrane element.

The separation membrane element, as shown in FIG. 3, has a rigid supporting plate 13 and a channel material 14 and the separation membrane 15 described above formed in that order on both faces thereof. The supporting plate 13 has dents 16 on both faces. The separation membrane 15 allows filtration of the fermentation culture solution. The channel material 14 is a material for transport of the filtrate from the separation membrane 15 efficiently to the supporting plate 13. The filtrate fed to the supporting plate 13 advances through the dent 16 of the supporting plate 13 into the water-collecting pipe 17 and is then discharged out of the continuous fermentation apparatus. A method such as head pressure difference, pump, suction filtration for example with liquid or gas, or pressurization of the apparatus system may be used as the power for discharging the filtrate.

Figure 4:
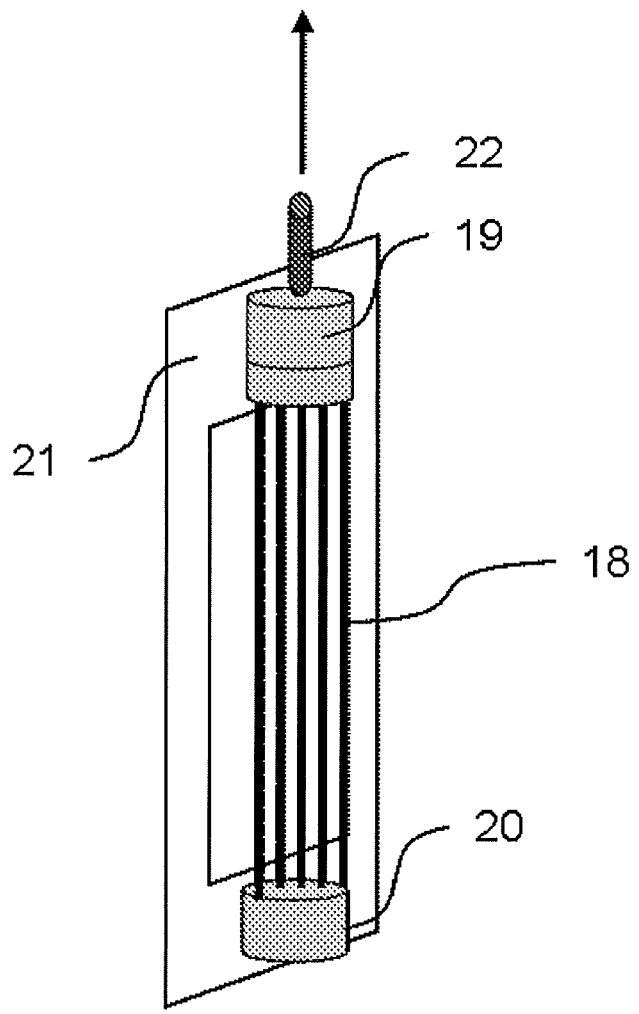
FIG. 4 is a schematic perspective view explaining another separation membrane element.

FIG. 4 is a schematic perspective view explaining another separation membrane element. The separation membrane element, as shown in FIG. 4, mainly has a bundle of hollow-fiber separation membranes 18 (porous membranes), a top resin-sealing layer 19 and a bottom resin-sealing layer 20. The separation membranes 18 are adhered and fixed to each other in the bundle shape by the top resin-sealing layer 19 and the bottom resin-sealing layer 20. The hollow regions of the hollow fiber membranes (porous membranes) of the separation membrane bundle 18 are sealed with the bottom resin-sealing layer 20 by adhesion and fixation in a structure preventing leakage of the culture solution. On the other hand, the top resin-sealing layer 19 does not seal the internal pores of the hollow fiber membranes (porous membranes) of the separation membrane bundle 18, as it is formed in a structure allowing flow of the filtrate into the water-collecting pipe 22. The separation membrane element may be installed in the continuous fermentation apparatus via the supporting frame 21. The fermentation product-containing filtrate filtered through the separation membrane bundle 18 advances through the hollow region of the hollow fiber membranes and the water-collecting pipe 22 and is discharged out of the continuous fermentation apparatus. A method such as head pressure difference, pump, suction filtration for example with liquid or gas or pressurization of the apparatus system may be used as the power for discharging the filtrate.

The member for the separation membrane element of the continuous fermentation apparatus used in the method of producing lactic acid is preferably a member resistant to high-pressure steam sterilization operation. If the continuous fermentation apparatus is sterilizable internally, it becomes possible to avoid the danger of undesired microbial contamination during continuous fermentation and perform more stabilized continuous fermentation. The member constituting the separation membrane element is preferably resistant to the condition of high-pressure steam sterilization operation, specifically at 121° C. for 15 minutes. For example, a metal such as stainless steel or aluminum or a resin such as polyamide resin, fluorine resin, polycarbonate resin, polyacetal resin, polybutylene terephthalate resin, PVDF, modified polyphenylene ether resin or polysulfone resin may be selected favorably for the separation membrane element member.

In the continuous fermentation apparatus used in the method of producing lactic acid, the separation membrane element may be installed in the fermentation reaction tank, as shown in FIG. 1, or outside the fermentation reaction tank, as shown in FIG. 2. If the separation membrane element is installed outside the fermentation reaction tank, a membrane separation tank may be installed separately and the separation membrane element installed therein, and the culture solution may be filtered continuously through the separation membrane element, as the culture solution is circulated between the fermentation reaction tank and the membrane separation tank.

In the continuous fermentation apparatus used in the method of producing lactic acid, the membrane separation tank is desirably sterilizable with high-pressure steam. If the membrane separation tank is sterilizable with high-pressure steam, contamination by undesired bacteria may be avoided easily.

Continuous fermentation, if carried out by the method of producing lactic acid by continuous fermentation, gives higher volumetric production rate and enables extremely efficient fermentation production, compared to batchwise fermentation. The fermentation production rate by continuous culture may be calculated according to the following Formula 3:

Fermentation production rate (g/L/hr)=Product concentration in discharged solution (g/L)×Discharge amount of fermentation culture solution (L/hr)/Amount of operational solution in apparatus (L)　　(Formula 3)

The fermentation production rate by batchwise culture may be calculated by dividing the amount of the product generated when the raw carbon source is all consumed (g) by the period needed for consumption of the carbon source (h) and the volume of the fermentation culture solution at the time (L).

The continuous culture is carried out, as it is stabilized, without deterioration in lactic acid yield and production rate for an extended period of time, by culturing a yeast having a lactate dehydrogenase-expressing cassette containing the promoter of a gene showing a gene expression amount larger by 5 times or more, preferably 7 times or more and more preferably 10 times or more, than the average relative expression amount of all genes after 50 hours from start of culture while filtering the yeast through a separation membrane, and thus, the continuous culture is preferably continued at least for 100 hours or more, preferably for 200 hours or more and more preferably for 300 hours or more.

Both D- and L-lactic acids may be provided.

Lactic acid obtained by the method of producing lactic acid may be provided mainly as a raw material for polylactic acid.

EXAMPLES

Hereinafter, favorable aspects will be described with reference to Examples, but it should be understood that this disclosure is not restricted at all by these Examples.

Reference Example 1

Preparation of Yeast Strain Having Lactic Acid-Producing Ability

A yeast containing the *Xenopus laevis*-derived ldh gene having the nucleotide sequence shown by SEQ ID No. 4 at a site downstream of PDC1 promoter was used as the yeast strain having a lactic acid-producing ability. The *Xenopus laevis*-derived ldh gene was cloned by PCR method. A phagemid DNA prepared from *Xenopus laevis* kideny-derived cDNA library (manufactured by STRATAGENE) according to the attached protocol was used as a template in PCR.

KOD-Plus polymerase (manufactured by Toyobo) was used for PCR amplification reaction, and the reaction buffer, dNTP mix and others used were those attached to the kit. 50 µL, of a reaction system containing 50 ng/sample of the phagemid DNA prepared according to the attached protocol as described above, 50 pmol/sample of primers and 1 unit/sample of KOD-Plus polymerase was prepared. The reaction solution was denatured at a temperature of 94° C. for 5 minutes in a PCR amplification system iCycler (manufactured by BIO-RAD), and then subjected to 30 cycles of heat denaturation at 94° C. for 30 seconds, primer annealing at 55° C. for 30 seconds and extension of complementary chain at 68° C. for 1 minute, and then cooled to a temperature of 4° C. The gene amplification primers (SEQ ID Nos. 7 and 8) were prepared so that a SalI-recognizing sequence is added to the 5 terminal side and a NotI-recognizing sequence to the 3 terminal side.

```
SEQ ID No. 7:
gtcgacatgg caactgtgaa ggataa

SEQ ID No. 8:
gcggccgcct agaactgcag ctcctt
```

The PCR amplification fragments were purified, and the terminals thereof were phosphorylated by T4 polynucleotide Kinase (manufactured by Takara Bio Inc.) and then ligated to pUC118 vector (which was previously cleaved with a restriction enzyme HincII and had the cut surface dephosphorylated). Ligation was carried out by using a DNA ligation kit Ver.2 (manufactured by Takara Bio Inc.). The ligation solution was transformed into competent cells of *E. coli* DH5α (manufactured by Takara Bio Inc.) and the mixture was seeded and cultured overnight on a LB plate containing an antibiotic ampicillin at a concentration of 50 µg/mL. Plasmid DNAs in the colonies obtained were collected by Miniprep and cleaved with restriction enzymes SalI and NotI, and plasmids containing the inserted *Xenopus laevis*-derived ldh gene were selected. All of the series of operations were carried out according to the attached protocol.

Figure 5:
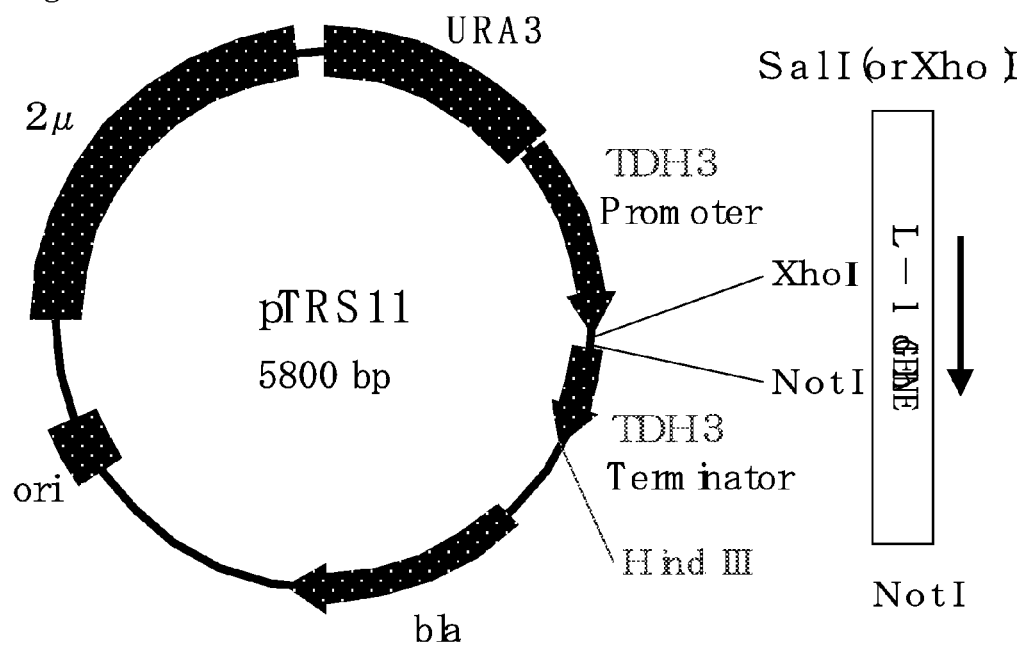
FIG. 5 is a chart explaining expression vector Ptrs11.

The pUC118 vectors containing the inserted *Xenopus laevis*-derived ldh gene were cleaved by restriction enzymes SalI and NotI; the DNA fragments were separated by 1% agarose gel electrophoresis; and the fragments containing the *Xenopus laevis*-derived ldh gene were purified by a common method. The fragments containing the ldh gene were ligated to the XhoI/NotI cleavage sites of the expression vector pTRS11 shown in FIG. 5; the plasmid DNAs were recovered by a method similar to that above; and an expression vector containing the inserted *Xenopus laevis*-derived ldh gene was selected by cleaving the expression vectors with restriction enzymes XhoI and NotI. Hereinafter, the expression vector containing the inserted *Xenopus laevis*-derived ldh gene thus prepared will be designated as pTRS102.

A 1.3 kb PCR fragment containing the *Xenopus laevis*-derived ldh gene and a TDH3 terminator sequence was amplified, by PCR using pTRS102 as amplification template and oligonucleotides (SEQ ID Nos. 9 and 10) as primer set. The oligonucleotide of SEQ ID No. 9 was designed to have a sequence corresponding to the 60 bp sequence upstream of the start codon of PDC1 gene.

SEQ ID No. 9:
tctcaattat tattttctac tcataacctc acgcaaaata acacagtcaa atcaatcaaa atggcaactg tgaaggataa actca SEQ ID No. 10:
aggcgtatca cgaggccctt Then, a 1.2 kb PCR fragment containing a yeast selectable marker TRP1 gene was amplified by PCR using plasmid pRS424 as amplification template and oligonucleotides (SEQ ID Nos. 11 and 12) as primer set. The oligonucleotide of SEQ ID No. 12 was designed to have an added sequence corresponding to the 60 bp sequence downstream from the termination codon of PDC1 gene.

SEQ ID No. 11:
gaattaattc ttgaagacga aagggcctcg tgatacgcct

SEQ ID No. 12:
agattgtact gagagtgcac tattttttcgt tacataaaaa tgcttataaa actttaacta ataattagag attaaatcgc ctgtgcggta tttcacaccg Each DNA fragment was isolated by 1% agarose gel electrophoresis and purified according to a common method. By PCR using a mixture of the 1.3 kb fragment and the 1.2 kb fragment thus obtained as amplification templates and oligonucleotides (SEQ ID Nos. 9 and 12) as primer set, an approximately 2.5 kb PCR fragment having sequences equivalent to the upstream and downstream 60 bp sequences of PDC1 gene respectively at the 5 and 3 terminals and containing *Xenopus laevis*-derived ldh gene, TDH3 terminator and TRP1 gene connected thereto was amplified.

The PCR fragments were isolated by 1% agarose gel electrophoresis and purified according to a common method; they are transformed into a yeast *Saccharomyces cerevisiae* NBRC10505 strain; and a transformant having the *Xenopus laevis*-derived ldh gene introduced on chromosome at a site downstream of the PDC1 gene promoter was selected by culture in a tryptophan-free medium.

The fact that the transformant thus obtained is a yeast having a *Xenopus laevis*-derived ldh gene introduced at a site downstream of the PDC1 gene promoter on chromosome was confirmed in the following manner: First, the genome DNA of the transformant was pre-pared with a genome DNA extraction kit Gentorukun (manufactured by Takara Bio Inc.) and production of amplified DNA fragment of approximately 2.8 kb was confirmed by PCR using the prepared genome DNA of the transformant as an amplification template and oligonucleotides (SEQ ID Nos, 12 and 13) as primer set. On the other hand, nontransformants gave amplified DNA fragments of approximately 2.1 kb by the PCR. Hereinafter, the transformant having the *Xenopus laevis*-derived ldh gene introduced at a site downstream of the PDC1 gene promoter on chromosome will be referred to as strain B2. The upstream and downstream sequences of the PDC1 gene can be obtained from the *Saccharomyces* Genome Database SEQ ID No. 13:
caaatatcgt ttgaatattt ttccg Subsequently, the yeast strain SW015 described in WO 2007/043253 pamphlet, in which the pdc 1 gene is replaced with the TRP1 marker and the pdc5 gene has a temperature-sensitive mutation, and the strain B2 obtained above were conjugated, to give a diploid cell. The diploid cell was forced to form ascus in an ascus-forming medium. The ascus was dissected with a micromanipulator; respective haploid cells were collected; and nutritional requirements of respective haploid cells were studied. Among the haploid cells obtained a strain having the *Xenopus laevis*-derived ldh gene inserted into the pdc1 gene locus and having a temperature-sensitive mutation in the pdc5 gene (not viable at 34° C.) was selected. The yeast strain was designated as strain SU014.

The fact that the strain SU014 had lactic acid-producing ability was confirmed by measuring the lactic acid contained in the supernatant of the culture of the transformant cells in medium (Methods in Yeast Genetics, 2000 Ed., CSHL Press) by HPLC under the following condition:

Column: Shim-Pack SPR-H (manufactured by Shimadzu Corp.)
Mobile phase: 5 mM p-toluenesulfonic acid (flow rate: 0.8 mL/min)
Reaction solution: 5 mM p-toluenesulfonic acid, 20 mM Bis-Tris, 0.1 mM
EDTA-2Na (flow rate: 0.8 mL/min)
Detection method: electrical conductivity
Temperature: 45° C.

The optical purity of L-lactic acid was determined by HPLC under the following condition:

Column: TSK-gel Enantio LI (registered trade name: manufactured by Toso Corporation)
Mobile phase: aqueous 1 mM copper sulfate solution
Flow rate: 1.0 ml/min
Detection method: UV254 nm
Temperature: 30° C.

The optical purity of L-lactic acid is calculated according to the following Formula:

Optical purity (%)=100×(L−D)/(L+D)

Herein, L represents the concentration of L-lactic acid, and D represents the concentration of D-lactic acid.

L-Lactic acid was detected and D-lactic acid was detected only in an amount of less than detection limit by HPLC analysis. The results above demonstrate that the strain SU014 has L-lactic acid-producing ability.

Reference Example 2

Method of Preparing Separation Membrane

A porous membrane prepared by the following method was used as the separation membrane.

A polyvinylidene fluoride (PVDF) resin was used as the resin, a polyethylene glycol (PEG) having a molecular weight of approximately 20,000 as the pore-forming agent, N,N-dimethylacetamide (DMAc) as the solvent and pure water as the nonsolvent, and these components were mixed under thorough agitation at a temperature of 90° C., to give a concentrated solution in the following composition:

PVDF: 13.0 wt %
PEG: 5.5 wt %
DMAc: 78.0 wt %
Pure water: 3.5 wt %

The concentrated solution was cooled to a temperature of 25° C. and then coated on a polyester fiber nonwoven fabric (porous base material) having a density of 0.48 g/cm³ and a thickness of 220 μm, and the resulting nonwoven fabric was immersed, immediately after application, in pure water at a temperature of 25° C. for 5 minutes and thrice in hot water at a temperature of 80° C. for wash out of DMAc and PEG, to give a porous membrane (separation membrane) having a porous resin layer. A range of 9.2 μm×10.4 μm on the surface of the porous resin layer on the side where the concentrated solution for separation membrane was coated was observed under scanning electron microscope at a magnification of 10,000 times, to show that the average diameter of all micropores observed was 0.02 μm. The pure water permeability of the separation membrane evaluated was $2 \times 10^{-9}$ m³/(m²·s·Pa). The water permeability was determined at a head height of 1 m, by using RO membrane-purified water at a temperature of 25° C. The standard deviation of the average micropore diameter was 0.0055 μm and the membrane surface roughness was 0.1 μm.

Reference Example 3

Filtration Continuous Culture of the Yeast Strain Having a Lactic Acid-Producing Ability by Using a Separation Membrane Filtration continuous culture was carried out by using the strain SU014 prepared in Reference Example 1 and the continuous culture apparatus shown in FIG. 1. A lactic acid fermentation medium in the composition shown in Table 1 was used as the medium. The medium was sterilized with high-pressure (2 atm) steam at a temperature of 121° C. for 15 minutes before use. Stainless steel and a polysulfone resin molding were used for the separation membrane element members and the porous membrane prepared in Reference Example 2 was used as the separation membrane. The operational condition in the present Example is as follows, unless specified otherwise:

Volume of reaction tank volume: 2 (L)
Volume of fermentation reaction tank: 1.5 (L)
Separation membrane used: PVDF filtration membrane (prepared in Reference Example 2)
Effective filtration area of membrane separation element: 120 cm²
Temperature adjusted to: 30 (° C.)
Ventilation rate of fermentation reaction tank: air: 0.01 (L/min), nitrogen gas: 0.19 (L/min)
Agitation velocity of fermentation reaction tank: 800 (rpm)
pH adjustment: adjusted to pH 5 with 1N NaOH
Antifoam: a sterilized antifoam PE-L (manufactured by Wako Pure Chemical Industries) added in an amount of 200 μL every 3 hours.

Sterilization: culture tank containing a separation membrane element and the medium used were all sterilized with high-pressure steam in an autoclave at 121° C. for 20 min.

TABLE 1

| | |
|---|---|
| Glucose | 100 g/L |
| Ammonium sulfate | 1.5 g/L |
| Yeast Nitrogen base w/o amino acid and ammonium sulfate (manufactured by Difco) | 1.7 g/L |
| 18 Standard amino acids excluding leucine and tryptophan | 152 mg/L |
| Leucine | 760 mg/L |
| Inositol | 152 mg/L |
| p-Aminobenzoic acid | 16 mg/L |
| Adenine | 40 mg/L |
| Uracil | 152 mg/L |

First, strain SU014 was cultured as shaken in a test tube containing 10 ml of a lactic acid fermentation medium overnight (preprepreculture). The culture solution obtained was transferred into 100 ml of a fresh lactic acid fermentation medium and the mixture was cultured as shaken in a 500-ml Sakaguchi flask for 24 hours at 30° C. (preculture). The preculture solution was seeded into 1.5 L of a lactic acid fermentation medium (glucose concentration: 70 g/L) placed in the continuous culture apparatus shown in FIG. 1, and the mixture was cultured for 24 hours, while the reaction tank 1 was agitated with an attached stirrer 5 at 400 rpm, as the ventilation rate, the temperature and the pH of the reaction tank 1 were adjusted (preculture). Immediately after the preculture, the lactic acid fermentation medium was supplied thereto continuously, and lactic acid was produced by continuous culture, while the membrane permeation amount was controlled to keep the fermentation solution amount in the continuous culture apparatus constant at 1.5 L. The concentrations of lactic acid produced and residual glucose in the membrane-permeated fermentation solution were determined as needed. The lactic acid/sugar yield and the lactic acid production rate were calculated from the amounts of generated lactic acid and the supplied raw glucose that was calculated from the glucose concentration. The glucose concentration was determined by using "Glucose Test Wako C" (registered trade name) (manufactured by Wako Pure Chemical Industries). As a result, it was found that, although the continuous culture continued consistently for a period of up to 200 hours, the lactic acid/sugar yield and the lactic acid production rate declined after about 200 hours, because of decrease of the concentration of lactic acid accumulated.

Example 1

Fluctuation of Gene Expression During Continuous Culture

For evaluation of fluctuation in gene expression during the continuous culture in Reference Example 3, the culture solution samples were obtained after 70 and 210 hours from the start of the continuous culture of Reference Example 3 and the total RNAs therein were extracted from the yeast. In extraction of the total RNA, the yeast obtained was suspended in 10 ml of a buffer solution for homogenization (50 mM sodium acetate (pH 5.3), 10 mM EDTA DEPC treated) to an $OD_{600}$ of 0.2 and the mixture was transferred into a 50 ml tube. 500 μL of 20% SDS was added thereto; 12 ml of phenol (saturated with homogenization buffer solution) previously warmed at 65° C. was added additionally thereto; and the mixture was agitated with a Voltex mixer for 5 seconds. The mixture was kept at 65° C. for 4 minutes and then cooled rapidly to room temperature in a dry ice/ethanol bath. It was centrifuged at room temperature (5 min. 12000 G); the aqueous supernatant was transferred into a separate 50 ml tube; and PCI (pH 5.3) in the same amount was added thereto for extraction. The aqueous supernatant was transferred into a separate 50 ml tube and chloroform in the same amount was added for extraction. The aqueous supernatant was transferred into a separate 50 ml tube; 3 M sodium acetate (pH 5.3) in 1/10 amount was added; and the mixture was subjected to ethanol precipitation. The resulting pellets obtained were washed twice with 80% ethanol, dried to solidness and dissolved in RNA-free water, to give a total RNA sample.

The concentration of the total RNA sample obtained was determined with an absorptiometer and 1 µg of the sample was used for DNA microarray analysis. The DNA microarray was carried out by using "3D-Gene" manufactured by Toray Industries Inc. according to the attached protocol. The scanner used was ScanArray Express (PerkinElmer), and scanning was performed under the condition of Cyanine 5 (PMT value: 55%) (for measurement of average fluorescence intensity after 210 hours of culture) or Cyanine 3 (PMT value: 70%) (for measurement of average fluorescence intensity after 70 hours of culture), to give an image. The fluorescence intensity of each spot in the image obtained was digitalized by GenePix Pro 5.0 software (Axon Instruments), and the median value was calculated. Then, the average fluorescence intensity of all spots in each sample was calculated.

As a result, CDC19 gene, IPP1 gene, ARF1 gene, CUPS gene, RPL28 gene, TRX2 gene, HSP104 gene, AHP1 gene, YMR122W-A, CIT1 gene, RPS15 gene, ALD4 gene, YPL225W, HSP26 gene, PGK1 gene, SED1 gene, MFA1 gene, HYP2 gene, HSP12 gene, QCR6 gene, HXK1 gene, TDH3 gene, ENO1 gene, BGL2 gene, YJL133C-A, QCR8 gene, FBA1 gene, CWP2 gene, CCW12 gene, TMA10 gene, SIP18 gene, HOR7 gene, CCW14 gene and PIR3 gene are confirmed in the sample after 70 hours of culture as genes having a fluorescence intensity larger by 10 times or more than the average fluorescence intensity, and CYS3 gene, CDC48 gene, LYS20 gene, HSP31 gene, ARG5,6 gene, RPS24A gene, RPL29 gene, RPL24A gene, ADH4 gene, MUP1 gene, RPL11B gene, THI4 gene, RPL24B gene, RPS0A gene, RPL27A gene, RPL16A gene, RPS21B gene, RPS5 gene, HOME gene, PDC5 gene, THI7 gene, MET17 gene, ECM40 gene, ARG1 gene, ZPS1 gene, IDH2 gene, CDC19 gene, IPP1 gene, ARF1 gene, RPL28 gene, TRX2 gene, HSP104 gene, AHP1 gene, CIT1 gene, RPS15 gene, ALD4 gene, YPL225X and CCW12 gene were confirmed in the sample after 210 hours of culture as genes having a fluorescence intensity larger by 10 times or more than the average fluorescence intensity. The results are summarized in Table 2.

TABLE 2

| 70-hr sample Name of gene | Average fluorescence intensity (Cyanine 3) = 2527 Fluorescence intensity | 210-hr sample Name of gene | Average fluorescence intensity (Cyanine 5) = 2560 Fluorescence intensity |
|---|---|---|---|
| CDC19 | 32744 | CYS3 | 31699 |
| IPP1 | 31010 | CDC48 | 48367 |
| ARF1 | 32791 | LYS20 | 26987 |
| CUP5 | 48892 | HSP31 | 65535 |
| RPL28 | 32227 | ARG5,6 | 25938 |
| TRX2 | 27127 | RPS24A | 25954 |
| HSP104 | 37404 | RPL29 | 31691 |

TABLE 2-continued

| 70-hr sample Name of gene | Average fluorescence intensity (Cyanine 3) = 2527 Fluorescence intensity | 210-hr sample Name of gene | Average fluorescence intensity (Cyanine 5) = 2560 Fluorescence intensity |
|---|---|---|---|
| AHP1 | 36389 | RPL24A | 27070 |
| YMR122W-A | 26689 | ADH4 | 29111 |
| CIT1 | 38065 | MUP1 | 36322 |
| RPS15 | 33355 | RPL11B | 42975 |
| ALD4 | 25334 | THI4 | 65535 |
| YPL225W | 33524 | RPL24B | 60397 |
| HSP26 | 65535 | RPS0A | 25985 |
| PGK1 | 45002 | RPL27A | 26846 |
| SED1 | 65535 | RPL16A | 30035 |
| MFA1 | 52959 | RPS21B | 41105 |
| HYP2 | 58791 | RPS5 | 26324 |
| HSP12 | 59804 | HOM6 | 46392 |
| QCR6 | 40818 | PDC5 | 65535 |
| HXK1 | 65535 | THI7 | 37815 |
| TDH3 | 44578 | MET17 | 65535 |
| ENO1 | 47131 | ECM40 | 35306 |
| BGL2 | 40588 | ARG1 | 25772 |
| YJL133C-A | 53171 | ZPS1 | 43966 |
| QCR8 | 65535 | IDH2 | 34806 |
| FBA1 | 56999 | CDC19 | 31238 |
| CWP2 | 65535 | IPP1 | 36610 |
| CCW12 | 65535 | ARF1 | 27340 |
| TMA10(reserved) | 52672 | RPL28 | 26537 |
| SIP18 | 57587 | TRX2 | 26762 |
| HOR7 | 50590 | HSP104 | 35829 |
| CCW14 | 27043 | AHP1 | 29875 |
| PIR3 | 40635 | CIT1 | 34931 |
|  |  | RPS15 | 38663 |
|  |  | ALD4 | 26524 |
|  |  | YPL225W | 27404 |
|  |  | CCW12 | 32536 |

The results identified the genes that are expressed in an amount larger by 10 times or more than the average relative expression amount of all genes after 50 hours from start of culture in continuous culture with simultaneous filtration of a yeast strain having a lactic acid-producing ability.

Example 2

Introduction of ldh Gene into SED1, CWP2 and ENO1 Gene Locuses

Based on the results obtained in Example 1, the ldh gene shown by SEQ ID No. 4 was introduced into the SED1 gene, CWP2 gene and ENO1 gene locuses.

In introduction thereof into the SED1 gene locus, a 1.3 kb PCR fragment containing the *Xenopus laevis*-derived ldh gene and the TDH3 terminator sequence was amplified by PCR using pTRS102 prepared in Reference Example 1 as amplification template and the oligonucleotides (SEQ ID Nos. 10 and 14) as primer set. The oligonucleotide of SEQ ID No. 14 was designed to add a sequence corresponding to the 60 bp sequence upstream of the start codon of SED1 gene.

SEQ ID No. 14:
tattgattta tagtcgtaac tacaaagaca agcaaaataa aatacgttcg ctctattaag atggcaactg tgaaggataa actca Then, an approximately 1.3 kb PCR fragment containing a yeast selectable marker HIS3 gene was amplified by PCR using the plasmid pRS423 as amplification template and oligonucleotides (SEQ ID Nos. 11 and 15) as primer set. The oligonucleotide of SEQ ID No. 15 was designed to add a sequence corresponding to the 60 bp sequence downstream the termination codon of SED1 gene.

SEQ ID No. 15:
aaaaaataac ataatactga aagaaagcat taagaaggcg gatgtgtcaa acaccaccgt ctgtgcggta tttcacaccg Each DNA fragment was separated by 1% agarose gel electrophoresis and purified by a common method. An approximately 2.6 kb PCR fragment having connected the *Xenopus laevis*-derived ldh gene, the TDH3 terminator and the HIS3 gene having added the sequences corresponding to the upstream and downstream 60-bp sequences of the SED1 gene respectively at the 5 and 3 terminals was amplified, by PCR using a mixture of two kinds of approximately 1.3 kb fragments thus obtained as amplification template and oligonucleotides (SEQ ID Nos. 14 and 15) as primer set.

The PCR fragment was separated by 1% agarose gel electrophoresis and purified by a common method, and then transformed into strain SU014, and a transformant having the *Xenopus laevis*-derived ldh gene incorporated at a site downstream of the SED1 gene promoter on chromosome was selected by culture in a histidine-free medium.

The fact that the transformant thus obtained is a yeast having the *Xenopus laevis*-derived ldh gene incorporated at a site downstream of the SED1 gene promoter on chromosome was confirmed in the following manner: First, the genome DNA of the transformant was prepared by using a genome DNA extraction kit Gentorukun (manufactured by Takara Bio Inc.) and production of an approximately 2.9 kb amplification DNA fragment was confirmed by PCR using it as amplification template and oligonucleotides (SEQ ID Nos. 16 and 17) as primer set. Nontransformants give an approximately 1.4 kb amplification DNA fragment by the PCR. Hereinafter, the transformant having the *Xenopus laevis*-derived ldh gene incorporated at a site downstream of the SED1 gene promoter on chromosome will be referred to as strain SU015.

SEQ ID No. 16:
tagattggcc gtaggggctg

SEQ ID No. 17:
cacgcaacgc gtaagaaaca

Subsequently, in introduction into the CWP2 gene locus, the 1.3 kb PCR fragment containing the *Xenopus laevis*-derived ldh gene and the TDH3terminator sequence was amplified, by PCR using the pTRS102 prepared in Reference Example 1 as amplification template and oligonucleotides (SEQ ID Nos. 10 and 18) as primer set. The oligonucleotide of SEQ ID No. 21 was designed to add a sequence corresponding to the 60 bp sequence upstream of the start codon of CWP2 gene.

SEQ ID No. 18:
cttctcataa tcaagaataa ataacttcat cacattcgct acacactaac aagaaaaaaa atggcaactg tgaaggataa actca Subsequently, the 1.3 kb PCR fragment containing a yeast selectable marker HIS3 gene was amplified by PCR using the plasmid pRS423 as amplification template and oligonucleotides (SEQ ID Nos. 11 and 19) as primer set. The oligonucleotide of SEQ ID No. 19 was designed to add a sequence corresponding to the 60 bp sequence downstream of the termination codon of CWP2 gene.

SEQ ID No. 19:
ctagtaaaac cgaaaatttt gaaaaaagcc atatagatat tataaaaaat cagagatttc ctgtgcggta tttcacaccg Each DNA fragment was separated by 1% agarose gel electrophoresis and purified by a common method. The approximately 2.6 kb PCR fragment having connected the *Xenopus laevis*-derived ldh gene, the TDH3 terminator and the HIS3 gene having added sequences corresponding to the 60 bp sequences upstream and downstream of the CWP2 gene respectively at the 5 and 3 terminals was amplified, by PCR using a mixture of the two kinds of approximately 1.3 kb fragments as amplification template and oligonucleotides (SEQ ID Nos. 18 and 19) as primer set.

The PCR fragment was separated by 1% agarose gel electrophoresis and purified by a common method; it is transformed into strain SU014; and a transformant strain having the *Xenopus laevis*-derived ldh gene incorporated at a site downstream of the CWP2 gene promoter on chromosome was selected by culture in a histidine-free medium.

The fact that the transformant thus obtained is a yeast having the *Xenopus laevis*-derived ldh gene incorporated at a site downstream of the CWP2 gene promoter on chromosome was confirmed in the following manner: First, the genome DNA of the transformant was prepared by using a genome DNA extraction kit Gentorukun (manufactured by Takara Bio Inc.), and it was found by PCR using it as an amplification template and oligonucleotides (SEQ ID Nos. 20 and 21) as primer set that an approximately 2.9 kb amplification DNA fragment was obtained. Nontransformants give an approximately 0.7 kb amplification DNA fragment by the PCR. Hereinafter, the transformant having the *Xenopus laevis*-derived ldh gene at a site downstream of the CWP2 gene promoter on chromosome will be referred to as strain SU016.

SEQ ID No. 20:
aaacagagaa atgtaacgtt

SEQ ID No. 21:
cattcgaaga gaaatcacag

Subsequently, in introduction into the ENO1 gene locus, a 1.3 kb PCR fragment containing the *Xenopus laevis*-derived ldh gene and the TDH3 terminator sequence was amplified, by PCR using the pTRS102 prepared in Reference Example 1 as amplification template and oligonucleotides (SEQ ID Nos. 10 and 22) as primer. The oligonucleotide of SEQ ID No. 22 was designed to add a sequence corresponding to the 60 bp sequence upstream of the start codon of ENO1 gene.

SEQ ID No. 22:
ctagctatttt ttcataaaaa accaagcaac tgcttatcaa cacacaaaca ctaaatcaaa atggcaactg tgaaggataa actca Subsequently, an approximately 1.3 kb PCR fragment containing a yeast selectable marker URA3 gene was amplified by PCR using the plasmid pRS426 as amplification template and oligonucleotides (SEQ ID Nos. 11 and 23) as primer set. The oligonucleotide of SEQ ID No. 23 was designed to add a sequence corresponding to the 60 bp sequence downstream of the termination codon of ENO1 gene.

SEQ ID No. 23:
gaaaatgaaa taaatgacaa aaaaacgtgt tttttggact agaaggctta atcaaaagct ctgtgcggta tttcacaccg Each DNA fragment was separated by 1% agarose gel electrophoresis and purified by a common method. An approximately 2.6 kb PCR fragment having connected the *Xenopus laevis*-derived ldh gene, the TDH3 terminator and the URA3 gene having added sequences corresponding to the 60 bp sequences upstream and downstream of EN01 gene respectively at the 5 and 3 terminals was amplified, by PCR using a mixture of the two kinds of 1.3 kb fragments obtained as an amplification template and oligonucleotides (SEQ ID Nos. 22 and 23) as primer set.

The PCR fragment was separated by 1% agarose gel electrophoresis and purified by a common method, and then transformed into the strain SU014, and a transformant having the *Xenopus laevis*-derived ldh gene incorporated at a site downstream of the promoter of ENO 1 gene on chromosome was selected by culture in an uracil-free medium.

The fact that the transformant thus obtained is a yeast having the *Xenopus laevis*-derived ldh gene incorporated at a site downstream of the promoter of EN01 gene on chromosome was confirmed in the following manner: First, the genome DNA of the transformant was prepared by using a genome DNA extraction kit Gentorukun (manufactured by Takara Bio Inc.), and an approximately 2.9 kb amplification DNA fragment was found to be prepared by PCR using it as amplification template and oligonucleotides (SEQ ID Nos. 24 and 25) as primer set. Nontransformants give an approximately 1.7 kb amplification DNA fragment by the PCR. Hereinafter, the transformant having the *Xenopus laevis*-derived ldh gene incorporated at a site downstream of the ENO1 gene on chromosome will be referred to as strain SU017.

SEQ ID No. 24:
aaggtatgcc tctccccgga

SEQ ID No. 25:
cggatacacg cgtcaccaca

Subsequently, the *Xenopus laevis*-derived ldh gene was introduced into the ENOL gene locus of strain SU015. Introduction of the *Xenopus laevis*-derived ldh gene into the EN01 gene locus of strain SU015 and confirmation thereof were carried out in a manner similar to the method described above, for preparation of the strain SU017, except that the strain SU014 was replaced with the strain SU015. The transformant obtained will be referred to as strain SU018.

Example 3

Preparation of Lactic Acid-Producing Yeast Strain 2

3-1 Cloning of human- and *Leuconostoc mesenteroides*-derived ldh genes

Then, the human- and *Leuconostoc mesenteroides*-derived ldh genes shown by SEQ ID Nos. 5 and 6 were cloned. First, the method of cloning the human-derived ldh gene will be described below:

A human breast cancer cell line (MCF-7) was cultured and recovered; the total RNA thereof was extracted by using TRIZOL Reagent (manufactured by Invitrogen); and cDNAs were prepared in reverse transcription reaction by using SuperScript Choice System (manufactured by Invitrogen) using the total RNA as template. These operations were performed in detail respectively according to the attached protocols. The cDNAs obtained were used as amplification templates in subsequent PCR.

The ldh gene was cloned by PCR by KOD-Plus-polymerase using the cDNAs obtained by the operations as amplification template and the oligonucleotides of SEQ ID Nos. 26 and 27 as primer set. Each PCR amplification fragment was purified; the terminal thereof was phosphorylated by T4 polynucleotide kinase (manufactured by Takara Shuzo Co., Ltd.) and ligated to a pUC118 vector (previously cleaved with restriction enzyme HincII and the cut surface dephosphorylated). The ligation was carried out by using a DNA ligation kit Ver.2 (manufactured by Takara Shuzo Co., Ltd.). A plasmid containing a subcloned human-derived ldh gene (accession number; AY009108, SEQ ID No. 5) was obtained by transforming *E. coli* DH5α with the ligated plasmid product and recovering the plasmid DNA. The pUC118 plasmid having the obtained ldh gene inserted therein was digested with restriction enzymes XhoI and NotI, and each DNA fragment obtained was inserted into a yeast expression vector pTRS11 at the XhoI/NotI cleavage sites, to give a human-derived ldh gene-expressing plasmid pTRS48.

Hereinafter, the method of cloning the *Leuconostoc mesenteroides*-derived ldh gene will be described.

The *Leuconostoc mesenteroides*-derived ldh gene was cloned by gene total synthesis to which the PCR method is applied, with reference to the sequence (SEQ ID No. 6) described in Res. Microbiol, 146, 291-302 (1995). The XhoI-recognizing sequence was added to the 5 terminal side and the NotI-recognizing sequence to the 3 terminal side during the total synthesis, and the PCR fragment was TA-cloned into the pTA2 vector. Ligation was carried out by using a DNA ligation kit Ver.2 (manufactured by Takara Shuzo Co., Ltd.). A plasmid having the subcloned *Leuconostoc mesenteroides*-derived ldh gene (SEQ ID No. 6) was obtained by transforming *E. coli* DH5α with the ligation plasmid product and recovering the plasmid DNA. The pTA2 plasmid containing the inserted ldh gene obtained was digested with restriction enzymes XhoI and NotI, and each DNA fragment obtained was inserted into the yeast expression vector pTRS11 at the XhoI/NotI cleavage site, to give a *Leuconostoc mesenteroides*-derived ldh gene-expressing plasmid pTRS152.

3-2 Introduction of Human- and *Leuconostoc mesenteroides*-Derived ldh Genes into Chromosome Subsequently, the ldh genes of SEQ ID Nos. 5 and 6 were introduced into the locuses of PDC1 gene, SED1 gene, CWP2 gene and ENO1 gene.

By PCR using plasmid pTRS48 and pTRS152 as amplification templates and the oligonucleotides of SEQ ID Nos. 28 and 10 (pTRS48) and SEQ ID Nos. 29 and 10 (pTRS152) as primer sets, a DNA fragment having the terminator sequences of 1.3 kb human-derived ldh gene and *Saccharomyces cerevisiae*-derived TDH3 gene and a DNA fragment containing the terminator sequences of *Leuconostoc mesenteroides*-derived ldh gene and the *Saccharomyces cerevisiae*-derived TDH3 gene were amplified. Also by PCR using the plasmid pRS424 as amplification template and the oligonucleotides of SEQ ID Nos. 11 and 12 as primer set, a DNA fragment containing a 1.2 kb *Saccharomyces cerevisiae*-derived TRP1 gene was amplified. Each DNA fragment was separated by 1.5% agarose gel electrophoresis and purified by a common method. Each of the products obtained by PCR using a mixture of the 1.3 kb fragment and the 1.2 kb fragment thus obtained as an amplification template and oligonucleotides of SEQ ID Nos. 28 and 12 and SEQ ID Nos. 29 and 12 as primer sets was separated by 1.5% agarose gel electrophoresis, and a 2.5 kb DNA fragment having a TRP1 gene connected to the human-derived LDH gene and a 2.5 kb DNA fragment having the TRP1 gene connected to the *Leuconostoc mesenteroides*-derived ldh gene were produced by a common method. A budding yeast strain NBRC10505 was transformed with the 2.5 kb DNA fragment by a common method, to be tryptophan-nonrequiring.

The fact that the transformant thus obtained is a yeast having the human-derived ldh gene or the *Leuconostoc mesenteroides*-derived ldh gene introduced at a site downstream of the promoter of PDC 1 gene on chromosome was confirmed by a method similar to the method of Reference Example 1.

Then, by a method similar to that in Reference Example 1, a yeast strain having the human- or *Leuconostoc mesenteroides*-derived ldh gene introduced at a site downstream of the PDC1 gene promoter on chromosome and having a temperature-sensitive mutation in the pdc5 gene were prepared. They will be referred to respectively as strains SU019 and SU024.

Introduction into the SED1, CWP2 and ENO1 gene locuses was performed by a method similar to that described in Example 2, except that the primers were altered. The primers altered will be described below.

Primer for Introduction into SED1 Gene Locus

PCR was conducted, as the primer shown by SEQ ID No. 30 was used, replacing the primer shown by SEQ ID No. 14 used in Example 2 in the case of human-derived ldh gene, and the primer shown by SEQ ID No. 33 was used in the case of the *Leuconostoc mesenteroides*-derived ldh gene, and the strains SU019 and SU024 were transformed, by using the PCR fragment obtained, respectively to be histidine-nonrequiring. The transformants obtained will be referred to respectively as strain SU020 (containing human-derived ldh gene introduced) and strain SU025 (containing *Leuconostoc mesenteroides*-derived ldh gene introduced).

Primer for Introduction into CWP2 Gene Locus

PCR was conducted, as the primer shown by SEQ ID No. 31 was used, replacing the primer shown by SEQ ID No. 18 used in Example 2 in the case of human-derived ldh gene and the primer shown by SEQ ID No. 34 was used in the case of the *Leuconostoc mesenteroides*-derived ldh gene, and the strains SU019 and SU024 were transformed, by using the PCR fragment obtained, respectively to be histidine-nonrequiring. The transformants obtained will be referred to respectively as strain SU021 (containing human-derived ldh gene introduced) and strain SU026 (containing *Leuconostoc mesenteroides*-derived ldh gene introduced).

Primer for Introduction into ENO1 Gene Locus

PCR was conducted, as the primer shown by SEQ ID No. 32 was used, replacing the primer shown by SEQ ID No. 22 used in Example 2 in the case of human-derived ldh gene and the primer shown by SEQ ID No. 35 was used in the case of the *Leuconostoc mesenteroides*-derived ldh gene, and the strains SU019 and SU024 were transformed, by using the PCR fragment obtained, respectively to be uracil-nonrequiring. The transformants obtained will be referred to respectively as strain SU022 (containing human-derived ldh gene introduced) and strain SU027 (containing *Leuconostoc mesenteroides*-derived ldh gene introduced). In addition, the strains SU020 and SU025 were transformed similarly to be uracil-nonrequiring, to give respectively strain SU023 (containing human-derived ldh gene introduced) and strain SU028 (containing *Leuconostoc mesenteroides*-derived ldh gene introduced).

Example 4

Lactic Acid Fermentation Test by Batch Culture

Lactic acid fermentation tests were carried out by batch culture, by using the strain obtained in Reference Example 1 (SU014) and strains SU015 to SU028 obtained in Examples 2 and 3. The lactic acid fermentation medium shown in Table 1 was placed in a 10 mL test tube, and each of the strains SU014 to SU028 in small amount was inoculated there, and the mixture was cultured overnight at 30° C. (preproculture). Then, 100 mL of the fresh lactic acid fermentation medium shown in Table 1 was placed in a 500-ml Erlenmeyer flask, and each preproculture solution was seeded there in the entire amount, and the mixture was cultured under agitation at 30° C. for 24 hours (preculture). Subsequently, each of the preculture solutions after preculture for 24 hours was added in the entire amount into a mini-jar fermenter (manufactured by Marubishi Bioengineering, volume: 5 L) containing 1 L of the lactic acid fermentation medium shown in Table 1, and the mixture was cultured at consistent agitation velocity (120 rpm), ventilation rate (0.1 L/min), temperature (30° C.) and pH (pH 5) (main culture). The solution was neutralized with 1N NaOH, and the feed rate was monitored by measuring weight change with a balance. The culture solution after main culture for 40 hours was centrifuged, and the supernatant obtained was filtered through membrane, the accumulated lactic acid concentration was calculated by the method described in Reference Example 1. The glucose concentration was determined by using "Glucose Test Wako C" (registered trade name, manufactured by Wako Pure Chemical Industries).

The lactic acid/sugar yields calculated from the measurement result are shown in Table 3. The optical purity of lactic acid was determined by the method described in Reference Example 1, showing that only L-lactic acid is detected and D-lactic acid was contained in an amount of less than detection limit in the case of strains SU014 to SU023, while only D-lactic acid was detected and L-lactic acid was contained in an amount of less than detection limit in the case of strains SU024 to SU028.

TABLE 3

| Lactic acid yield (%) | Strain name | SU014 | SU015 | SU016 | SU017 | SU018 | SU019 | SU020 | SU021 |
|---|---|---|---|---|---|---|---|---|---|
| | | 53 | 58 | 57 | 61 | 62 | 40 | 45 | 43 |
| | Strain name | SU022 | SU023 | SU024 | SU025 | SU026 | SU027 | SU028 | |
| | — | 47 | 49 | 38 | 42 | 40 | 44 | 45 | |

The results confirmed that, in continuous culture with simultaneous filtration of a yeast strain having a lactic acid-producing ability, lactic acid is obtained at a yield higher by the strains SU015 to SU018 (*Xenopus laevis*-derived ldh gene-introduced strains), the strains SU020 to 024 (human-derived ldh gene-introduced strains) and the strains SU025 to 028 (*Leuconostoc mesenteroides*-derived ldh gene-introduced strains), i.e., yeasts having an introduced lactate dehydrogenase-expressing cassette having a ldh gene at a site downstream of the promoter of a gene having an expression amount larger by 10 times or more than the average relative expression amount of all genes after 50 hours from start of culture, than by the strains SU014, SU019 and SU024.

Example 5

Lactic Acid Fermentation Test by Continuous Culture

Filtration continuous culture was carried out in the continuous culture apparatus shown in FIG. 1, by using the transformant yeast strains SU015 to SU028 obtained in Examples 2 and 3. The medium used was a lactic acid fermentation medium in the composition shown in Table 1, of which the glucose concentration was changed to 70 g/L. The medium was sterilized by high-pressure steam (2 atm.) at a temperature of 121° C. for 15 minutes before use. Stainless steel and a polysulfone resin molding were used for the separation membrane element members. The separation membrane used was the porous membrane prepared in Reference Example 2. The operational condition in the present Example is as follows, unless specified otherwise:

- Volume of reaction tank: 2 (L)
- Volume of fermentation reaction tank: 1.5 (L)
- Separation membrane used: PVDF filtration membrane (prepared in Reference Example 2)
- Effective filtration area of membrane separation element: 120 $cm^2$
- Temperature adjusted to: 30 (° C.)
- Ventilation rate of fermentation reaction tank: air: 0.01 (L/min), nitrogen gas: 0.19 (L/min)
- Agitation velocity of fermentation reaction tank: 800 (rpm)
- pH adjustment: adjusted to pH 5 with 5N calcium hydroxide
- Antifoam: an sterilized antifoam PE-L (manufactured by Wako Pure Chemical Industries) was added in an amount of 200 μL every 3 hours
- Sterilization: the culture tank including separation membrane elements and the medium used were all sterilized under high-pressure stem in an autoclave at 121° C. for 20 min.

First, each of the strains SU015 to SU028 was cultured overnight in a test tube containing 10 ml of the lactic acid fermentation medium shown in Table 1 (preprepreculture). The culture solution obtained was seeded in the entire amount to 100 ml of the fresh lactic acid fermentation medium shown in Table 1 and the mixture was cultured under agitation in a 500-ml Sakaguchi flask for 24 hours at 30° C. (preculture). The preculture solution was added to 1.5 L of the lactic acid fermentation medium in the continuous culture apparatus shown in FIG. 1, and the mixture was cultured for 24 hours, while the reaction tank 1 was agitated by an attached stirrer 5 at 400 rpm and the ventilation rate, temperature and pH of the reaction tank 1 were adjusted (preculture). Immediately after the preculture, the lactic acid fermentation medium was supplied continuously thereto, and lactic acid was produced by continuous culture, while the membrane permeation amount was controlled to make the volume of the fermentation solution in the continuous culture apparatus kept constant at 1.5 L. The concentrations of lactic acid produced and residual glucose in the membrane-permeated fermentation solution were monitored as needed. The accumulated lactic acid concentration was determined by the method described in Reference Example 1 and the glucose concentration was determined by using "Glucose Test Wako C" (registered trade name, manufactured by Wako Pure Chemical Industries).

The lactic acid/sugar yield and the lactic acid production rate, as calculated from lactic acid and the glucose supplied calculated from the glucose concentration, are summarized in Tables 4 and 5, together with the results obtained in Reference Example 1. Calculation was made according to Formula 3, and the time in the Table is the time elapsed after start of culture.

TABLE 4

| | Strain name | Lactic acid yield (%) | | | | |
|---|---|---|---|---|---|---|
| | | 50-100 hours | 100-150 hours | 150-200 hours | 200-250 hours | 250-300 hours |
| Reference Example 1 | SU014 | 65 | 75 | 66 | 45 | 20 |
| Example 4 | SU015 | 68 | 73 | 72 | 70 | 67 |
| | SU016 | 67 | 74 | 72 | 69 | 65 |
| | SU017 | 70 | 73 | 75 | 73 | 70 |
| | SU018 | 75 | 80 | 82 | 82 | 79 |
| | SU019 | 51 | 63 | 57 | 38 | 18 |
| | SU020 | 54 | 65 | 63 | 60 | 62 |
| | SU021 | 53 | 62 | 62 | 58 | 56 |
| | SU022 | 57 | 66 | 68 | 65 | 63 |
| | SU023 | 60 | 70 | 68 | 68 | 70 |
| | SU024 | 45 | 54 | 50 | 33 | 15 |
| | SU025 | 48 | 58 | 55 | 54 | 56 |
| | SU026 | 48 | 57 | 55 | 53 | 52 |
| | SU027 | 50 | 60 | 59 | 59 | 57 |
| | SU028 | 52 | 63 | 64 | 61 | 62 |

TABLE 5

| | Strain name | Lactic acid production rate (g/L/h) | | | | | |
|---|---|---|---|---|---|---|---|
| | | 50 hours | 100 hours | 150 hours | 200 hours | 250 hours | 300 hours |
| Reference Example 1 | SU014 | 2.5 | 3.1 | 3.1 | 2.6 | 1.7 | 0.8 |
| Example 4 | SU015 | 2.9 | 3.1 | 3 | 3 | 2.8 | 2.5 |
| | SU016 | 2.9 | 3 | 3 | 3 | 2.8 | 2.5 |
| | SU017 | 2.9 | 3.1 | 3.1 | 3.1 | 3 | 2.9 |
| | SU018 | 3.1 | 3.3 | 3.4 | 3.4 | 3.4 | 3.2 |
| | SU019 | 1.8 | 2.0 | 2.3 | 2.1 | 1.4 | 0.5 |
| | SU020 | 1.9 | 2.2 | 2.5 | 2.4 | 2.3 | 2.4 |
| | SU021 | 2.0 | 2.2 | 2.3 | 2.2 | 2.0 | 1.9 |
| | SU022 | 2.1 | 2.4 | 2.6 | 2.5 | 2.4 | 2.4 |
| | SU023 | 2.2 | 2.6 | 2.7 | 2.7 | 2.6 | 2.7 |
| | SU024 | 1.4 | 1.6 | 1.8 | 1.7 | 1.2 | 0.5 |
| | SU025 | 1.6 | 2.0 | 2.1 | 1.9 | 1.8 | 1.9 |
| | SU026 | 1.6 | 1.8 | 1.9 | 1.9 | 1.8 | 1.8 |
| | SU027 | 1.7 | 2.1 | 2.2 | 2.0 | 2.0 | 1.9 |
| | SU028 | 1.8 | 2.3 | 2.4 | 2.3 | 2.2 | 2.2 |

The results showed that, in continuous culture with simultaneous filtration of a yeast strain having a lactic acid-producing ability, lactic acid can be produced at high yield and high production rate consistently for up to 300 hours by the strains SU015 to SU018, strains SU020 to SU023 and strains SU025 to SU028, i.e., yeasts having an introduced lactate dehydrogenase-expressing cassette having a ldh gene at a site downstream of the promoter of a gene having an expression amount larger by 10 times or more than the average relative expression amount of all genes after 50 hours from start of culture. On the other hand, the yield and the lactic acid production rate declined rapidly after 200 hours, when the strain of Reference Example 1 (SU014) or a strain SU019 or SU024 was used. In addition, measurement of the optical purity of each sample by the method described in Reference Example 1 showed that only L-lactic acid is detected and D-lactic acid is present in an amount less than detection limit in the case of strains SU014 to SU023, while only D-lactic acid is detected and L-lactic acid is present in an amount less than detection limit in the case of strains SU024 to SU028.

What is claimed is:

1. An isolated expression cassette, comprising a gene encoding a lactate dehydrogenase connected to a site downstream of a promoter, wherein the promoter is a promoter of a SED1 gene consisting of the base sequence shown by SEQ ID NO: 1.

2. A transformed yeast strain, comprising at least one expression cassette according to claim 1, integrated into a chromosome.

3. The transformed yeast strain according to claim 2, wherein at least one gene thereof selected from suppression-of-exponential-defect 1 gene (SED1 gene), cell-wall-associated protein 2 gene (CWP2 gene) and enolase 1 gene (ENO1 gene) is substituted with the expression cassette.

4. The transformed yeast strain according to claim 2, wherein the transformed yeast strain belongs to the genus *Saccharomyces*.

5. The transformed yeast strain according to claim 2, wherein the transformed yeast strain is *Saccharomyces cerevisiae*.

6. A method of producing lactic acid, comprising a culture step of culturing the transformant yeast strain according to claim 2.

7. The method of producing lactic acid according to claim 6, wherein the culture step is a continuous fermentation comprising filtering a culture solution through a separation membrane, recovering lactic acid from resulting filtrate, holding or feeding back unfiltered solution to the culture solution, and adding medium to the culture solution.

* * * * *

SEQUENCE LISTING

<160> NUMBER OF SEQ ID NOS: 35

<210> SEQ ID NO 1
<211> LENGTH: 1000
<212> TYPE: DNA
<213> ORGANISM: Saccharomyces cerevisiae

<400> SEQUENCE: 1

```
aggattttaa tctgttggag ttaaggtgaa tacgtttttc catattgggg tatgcagctc      60
gaacctaaag tggtatgtac acatcccctc aagcacaccc attacccttta taggattaat     120 gtaagcaaca gcttacacgg aattggaaat actattcaac gatccatgca tctgccagat     180
tcggacatgc atattcccca attggatata gaaaattaac gtaaggcagt atcttttcac     240
aatgtacttg caacgcggcg acttaaagtt gaagtacaac ctgcagcagc ggcttttgt      300 acggtacgcc aaactgtcaa tggataatat tgcgtagacc gaaaaaggta atcctcaaca     360
ctacccgtgg tggatgacct aaagcagtaa tattggttgg aattatctcc cagacggcac     420 cgtctcccg agaaagctta gccccgaggt ctaccttcca tacaccactg attgctccac      480
gtcatgcggc cttctttcga ggacaaaaag gcatatatcg ctaaaattag ccatcagaac     540
cgttattgtt attatatttt cattacgaaa gaggagaggg cccagcgcgc cagagcacac     600
acggtcattg attactttat ttggctaaag atccatcct tctcgatgtc atctctttcc       660
attcttgtgt attttgatt gaaatgatt ttttgtccac taatttctaa aaataagaca       720
aaaagccttt aagcagtttt tcatccattt tactacggta aaatgaatta gtacggtatg     780
gctcccagtc gcattatttt tagattggcc gtaggggctg gggtagaact agagtaagga     840
acattgctct gccctctttt gaactgtcat ataaatacct gacctatttt attctccatt     900
atcgtattat ctcacctctc tttttctatt ctcttgtaat tattgattta tagtcgtaac     960
tacaaagaca agcaaaataa aatacgttcg ctctattaag                          1000
```

<210> SEQ ID NO 2
<211> LENGTH: 1000
<212> TYPE: DNA
<213> ORGANISM: Saccharomyces cerevisiae

<400> SEQUENCE: 2

```
ctaatagaca aggtgctatg agtgaattgc tagcctcccc ttttattt gtgcggtcac        60 cgcaagggac aaagctttc ttagaaaacc gtctgagaag cataacgtac gccatcccct     120
agacatatta ataatgctac agatactatg ctgctcgtct tttttgacg acccttttat     180 tgcaatgtgc aactaatggc aaacaaccac atagtatcac agtattacat tgcctccacc     240
gatgcggatg ttagggcgcc aagtctgtca tgaagcatgt tcctgtcata atcttgtatg     300
caaaataccg cgttctgcgc cactgatatg ctaggcagca gcaacctatg cagaagattg     360
cttttcccac gcctgtttta cgtctccagg gcacttgaaa caatgcagcg atcgccgcca     420
caacacgcca aagagaagcg aaagtgggcc tgggcggcct cagtttcggc agaggtaaac     480
aacacgaact gaactgcctt agctccgaag ggcaattcca caggcactcc gcggggcccg     540
gccaaggccc aaaaggcgtg gaatatgcgc gttttgggc cataacaccc agtaccacgg     600
ccggaacggg ccatataata agttttttcac tctcaagaat ggtaaacgta aataggaaca     660
tcccactacc ctagaaattg cggaaatttc gcgcttatca ttagaaaatc tggaaccgtc     720
ctttttcctc tttcttgcat ttccctttcc gtattattgc cattcttttaa ctgcatttgg    780 ggaaccgtag accaaaagcc aaacagagaa atgtaacgtt ctaaaaaaaa aacaacgaaa     840
```

| | | |
|---|---|---|
| aaattgaaaa ataagataca ataatcgtat ataaatcagg cttcttgttc atcattttca | 900 | |
| attctcttct tgccatccct tttcctatct ttgttctttt cttctcataa tcaagaataa | 960 | |
| ataacttcat cacattcgct acacactaac aagaaaaaaa | 1000 | |

<210> SEQ ID NO 3
<211> LENGTH: 1000
<212> TYPE: DNA
<213> ORGANISM: Saccharomyces cerevisiae

<400> SEQUENCE: 3

| | | |
|---|---|---|
| tagaaagcat actatactat tcgacacttc ctttcaatcc tggaattaac agtcacttt | 60 | |
| aaaaaagaca tctaccgtga aggtgccgta gagtatcgcg ttaccatatc gccaaaaact | 120 | |
| gatatacgcc gcggaaacca ggcaaacaat tgaaaagaaa aattttgagg aactctctgc | 180 | |
| atcgaagccg tctagagtta ccactagtca gatgccgcgg gcacttgagc acctcatgca | 240 | |
| cagcaataac acaacacaat ggttagtagc aacctgaatt cggtcattga tgcatgcatg | 300 | |
| tgccgtgaag cgggacaacc agaaaagtcg tctataaatg ccggcacgtg cgatcatcgt | 360 | |
| ggcggggttt taagagtgca tatcacaaat tgtcgcatta ccgcggaacc gccagatatt | 420 | |
| cattacttga cgcaaaagcg tttgaaataa tgacgaaaaa gaaggaagaa aaaaaagaa | 480 | |
| aaataccgct tctaggcggg ttatctactg atccgagctt ccactaggat agcacccaaa | 540 | |
| cacctgcata tttggacgac ctttacttac accaccaaaa accactttcg cctctcccgc | 600 | |
| ccctgataac gtccactaat tgagcgatta cctgagcggt cctcttttgt ttgcagcatg | 660 | |
| agacttgcat actgcaaatc gtaagtagca acgtctcaag gtcaaaactg tatggaaacc | 720 | |
| ttgtcacctc acttaattct agctagccta ccctgcaagt caagaggtct ccgtgattcc | 780 | |
| tagccacctc aaggtatgcc tctccccgga aactgtggcc ttttctggca cacatgatct | 840 | |
| ccacgatttc aacatataaa tagcttttga taatggcaat attaatcaaa tttattttac | 900 | |
| ttctttcttg taacatctct cttgtaatcc cttattcctt ctagctattt ttcataaaaa | 960 | |
| accaagcaac tgcttatcaa cacacaaaca ctaaatcaaa | 1000 | |

<210> SEQ ID NO 4
<211> LENGTH: 999
<212> TYPE: DNA
<213> ORGANISM: Xenopus laevis

<400> SEQUENCE: 4

| | | |
|---|---|---|
| atggcaactg tgaaggataa actcatccac aatgtggtca aggaggagtc gctcccccag | 60 | |
| aacaaggtca ccattgtggg tgtgggggcc gtgggcatgg cctgtgccat cagtgtcctg | 120 | |
| cagaaggatt tggcagatga gcttgcactt gttgatgtga tagaagacaa actgaagggg | 180 | |
| gaaatgatgg atctccagca tggcagtctg ttccttcgta cccccaagat tgtctcaggg | 240 | |
| aaagattaca gcgtcactgc aaactccaag ctggtagttg tgacggccgg ggcccgtcag | 300 | |
| caggagggag agagtcgcct gaatctggtt cagcgcaatg tcaacatctt caaattcatc | 360 | |
| attcccaaca ttgtcaagta cagccccaac tgcaccctgc tcatcgtctc caacccagtg | 420 | |
| gacattctga catatgtggc ctggaagatc agtggattcc ccaaaaaccg tgtcattggc | 480 | |
| agcggctgca atttggactc tgcccgtttc cgttacctca tggggcagaa gtttgggatc | 540 | |
| cacacccaga gctgccacgg ttgggtcatt ggggaacacg gagactcgag tgtgccagtg | 600 | |
| tggagtgggg tgaatgtggc tggcgtgtcc ctgaaaaccc tgcaccccga tattgggagt | 660 | |

| | |
|---|---|
| gacgcagaca aggagaactg gaaggaggtg cacaagcagg ttgtggacag cgcctatgaa | 720 |
| gtgatcaagc tgaagggcta cacctcctgg gctattggcc tgtccgtagc tgacctgtct | 780 |
| gagagtatcc tgaagaacct ccgccgagtc catcccattt ccacaatggt caagggcatg | 840 |
| tacggcgtga ataatgatgt tttcctcagt gtccctgtg tgttgggcaa cttgggcatc | 900 |
| acagacgtgg ttaacatgac gctgaaggca gatgaagagg atcgcttacg caagagcgca | 960 |
| gacacccctgt gggccatcca aaggagctg cagttctag | 999 |

<210> SEQ ID NO 5
<211> LENGTH: 999
<212> TYPE: DNA
<213> ORGANISM: Homo sapiens

<400> SEQUENCE: 5

| | |
|---|---|
| atggcaactc taaaggatca gctgatttat aatcttctaa aggaagaaca gacccccag | 60 |
| aataagatta cagttgttgg ggttggtgct gttggcatgg cctgtgccat cagtatctta | 120 |
| atgaaggact tggcagatga acttgctctt gttgatgtca tcgaagacaa attgaaggga | 180 |
| gagatgatgg atctccaaca tggcagcctt ttccttagaa caccaaagat tgtctctggc | 240 |
| aaagactata atgtaactgc aaactccaag ctggtcatta tcacggctgg ggcacgtcag | 300 |
| caagagggag aaagccgtct taatttggtc cagcgtaacg tgaacatatt taaattcatc | 360 |
| attcctaatg ttgtaaaata cagcccgaac tgcaagttgc ttattgtttc aaatccagtg | 420 |
| gatatcttga cctacgtggc ttggaagata agtggttttc ccaaaaaccg tgttattgga | 480 |
| agtggttgca atctggattc agcccgattc cgttacctga gggggaaaag gctgggagtt | 540 |
| cacccattaa gctgtcatgg gtgggtcctt ggggaacatg agattccag tgtgcctgta | 600 |
| tggagtggaa tgaatgttgc tggtgtctct ctgaagactc tgcacccaga tttagggact | 660 |
| gataaagata aggaacagtg gaaagaggtt cacaagcagg tggttgagag tgcttatgag | 720 |
| gtgatcaaac tcaaaggcta cacatcctgg gctattggac tctctgtagc agatttggca | 780 |
| gagagtataa tgaagaatct taggcgggtg cacccagttt ccaccatgat taagggtctt | 840 |
| tacggaataa aggatgatgt cttccttagt gttcctggca ttttgggaca gaatggaatc | 900 |
| tcagaccttg tgaaggtgac tctgacttct gaggaagagg cccgtttgaa gagagtgca | 960 |
| gatacacttt gggggatcca aaggagctg caattttaa | 999 |

<210> SEQ ID NO 6
<211> LENGTH: 996
<212> TYPE: DNA
<213> ORGANISM: Leuconostoc mesenteroides

<400> SEQUENCE: 6

| | |
|---|---|
| atgaagattt ttgcttacgg cattcgtgat gatgaaaagc catcacttga agaatggaaa | 60 |
| gcggctaacc cagagattga agtggactac acacaagaat tattgacacc tgaaacagct | 120 |
| aagttggctg agggatcaga ttcagctgtt gtttatcaac aattggacta tacacgtgaa | 180 |
| acattgacag ctttagctaa cgttggtgtt actaacttgt cattgcgtaa cgttggtaca | 240 |
| gataacattg attttgatgc agcacgtgaa tttaacttta acatttcaaa tgttcctgtt | 300 |
| tattcaccaa atgctattgc agaacactca atgcttcaat tatctcgttt gctacgtcgc | 360 |
| acgaaagcat tggatgccaa aattgctaag cgagacttgc gttgggcacc aacaactgga | 420 |
| cgtgaaatgc gtatgcaaac agttggtgtt attggtacag gtcatattgg ccgtgttgct | 480 |
| attaacattt tgaaaggctt tggggccaag gttattgctt atgacaagta cccaaatgct | 540 |

```
gaattacaag cagaaggttt gtacgttgac acattagacg aattatatgc acaagctgat    600
gcaatttcat tgtatgttcc tggtgtacct gaaaaccatc atctaatcaa tgcagatgct    660
attgctaaga tgaaggatgg tgtggttatc atgaacgctg cgcgtggtaa tttgatggac    720
attgacgcta ttattgatgg tttgaattct ggtaagattt cagacttcgg tatggacgtt    780
tatgaaaatg aagttgcttg ttcaatgaag attggtctgg taaagaattc cccagatgct    840
aagattgctg acttgattgc acgcgaaaat gttatgatca ccccacacac ggctttctat    900
acaactaaag ctgttctaga aatggttcac caatcatttg atgcagcagt tgctttcgcc    960
aagggtgaga agccagctat tgctgttgaa tattaa                              996
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcgacatgg caactgtgaa ggataa                                          26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggccgcct agaactgcag ctcctt                                          26

<210> SEQ ID NO 9
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctcaattat tattttctac tcataacctc acgcaaaata acacagtcaa atcaatcaaa    60
atggcaactg tgaaggataa actca                                          85

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggcgtatca cgaggccctt                                                 20

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaattaattc ttgaagacga aagggcctcg tgatacgcct agattgtact gagagtgcac    60

<210> SEQ ID NO 12
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tatttttcgt tacataaaaa tgcttataaa actttaacta ataattagag attaaatcgc    60
ctgtgcggta tttcacaccg                                                80

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caaatatcgt ttgaatattt ttccg                                          25

<210> SEQ ID NO 14
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tattgattta tagtcgtaac tacaaagaca agcaaaataa aatacgttcg ctctattaag    60
atggcaactg tgaaggataa actca                                          85

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaaaataac ataatactga aagaaagcat taagaaggcg gatgtgtcaa acaccaccgt    60
ctgtgcggta tttcacaccg                                                80

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tagattggcc gtagggctg                                                 20

<210> SEQ ID NO 17
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cacgcaacgc gtaagaaaca                                                      20

<210> SEQ ID NO 18
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttctcataa tcaagaataa ataacttcat cacattcgct acacactaac aagaaaaaaa          60
atggcaactg tgaaggataa actca                                                85

<210> SEQ ID NO 19
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctagtaaaac cgaaaatttt gaaaaaagcc atatagatat tataaaaaat cagagatttc          60
ctgtgcggta tttcacaccg                                                      80

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaacagagaa atgtaacgtt                                                      20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cattcgaaga gaaatcacag                                                      20

<210> SEQ ID NO 22
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctagctattt ttcataaaaa accaagcaac tgcttatcaa cacacaaaca ctaaatcaaa          60
```
atggcaactg tgaaggataa actca                                            85

<210> SEQ ID NO 23
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaaaatgaaa taaatgacaa aaaaacgtgt tttttggact agaaggctta atcaaaagct      60
ctgtgcggta tttcacaccg                                                  80

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaggtatgcc tctccccgga                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggatacacg cgtcaccaca                                                  20

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcgagatgg caactctaaa ggatca                                           26

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcggccgctt aaaattgcag ctcctttt                                         28

<210> SEQ ID NO 28
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
tctcaattat tattttctac tcataacctc acgcaaaata acacagtcaa atcaatcaaa      60
atggcaactc taaaggatca gctga                                           85

<210> SEQ ID NO 29
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tctcaattat tattttctac tcataacctc acgcaaaata acacagtcaa atcaatcaaa      60
atgaagattt ttgcttacgg cattc                                           85

<210> SEQ ID NO 30
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tattgattta tagtcgtaac tacaaagaca agcaaaataa aatacgttcg ctctattaag      60
atggcaactc taaaggatca gctga                                           85

<210> SEQ ID NO 31
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cttctcataa tcaagaataa ataacttcat cacattcgct acacactaac aagaaaaaaa      60
atggcaactc taaaggatca gctga                                           85

<210> SEQ ID NO 32
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctagctattt ttcataaaaa accaagcaac tgcttatcaa cacacaaaca ctaaatcaaa      60
atggcaactc taaaggatca gctga                                           85

<210> SEQ ID NO 33
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgaagattt tgcttacgg cattctattg atttatagtc gtaactacaa agacaagcaa       60
aataaaatac gttcgctcta ttaag                                           85
```

```
<210> SEQ ID NO 34
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atgaagattt ttgcttacgg cattccttct cataatcaag aataaataac ttcatcacat    60
tcgctacaca ctaacaagaa aaaaa                                          85

<210> SEQ ID NO 35
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgaagattt ttgcttacgg cattcctagc tatttttcat aaaaaaccaa gcaactgctt    60
atcaacacac aaacactaaa tcaaa                                          85
```